(12) United States Patent
Steuer et al.

(10) Patent No.: US 6,873,865 B2
(45) Date of Patent: *Mar. 29, 2005

(54) METHOD AND APPARATUS FOR NON-INVASIVE BLOOD CONSTITUENT MONITORING

(75) Inventors: Robert R. Steuer, Pleasant View, UT (US); David R. Miller, Morgan, UT (US)

(73) Assignee: Hema Metrics, Inc., Kaysville, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/733,236

(22) Filed: Dec. 12, 2003

(65) Prior Publication Data

US 2004/0127779 A1 Jul. 1, 2004

Related U.S. Application Data

(63) Continuation of application No. 09/771,596, filed on Jan. 30, 2001, now Pat. No. 6,671,528, which is a continuation of application No. 09/244,756, filed on Feb. 5, 1999, now Pat. No. 6,181,958.
(60) Provisional application No. 60/073,784, filed on Feb. 5, 1998.

(51) Int. Cl.$^7$ .............................................. A61B 5/00
(52) U.S. Cl. ..................................................... 600/322
(58) Field of Search ................................ 600/322, 323, 600/328, 326, 330, 336, 310

(56) References Cited

U.S. PATENT DOCUMENTS

| | | |
|---|---|---|
| 4,802,486 A | 2/1989 | Goodman et al. |
| 5,099,841 A | 3/1992 | Heinonen et al. |
| 5,111,817 A | 5/1992 | Clark et al. |
| 5,372,136 A | 12/1994 | Steuer et al. |
| 5,499,627 A * | 3/1996 | Steuer et al. ............... 600/322 |
| 5,638,816 A | 6/1997 | Kiani-Azarbayjany et al. |
| 5,791,348 A | 8/1998 | Aung et al. |
| 6,181,958 B1 * | 1/2001 | Steuer et al. ............... 600/322 |

FOREIGN PATENT DOCUMENTS

EP          0 444 934 A1    1/1990

* cited by examiner

Primary Examiner—Eric F. Winakur
Assistant Examiner—Matthew Kremer
(74) Attorney, Agent, or Firm—Jacobson Holman PLLC

(57) ABSTRACT

A system for determining a biologic constituent including hematocrit transcutaneously, noninvasively and continuously. A finger clip assembly includes including at least a pair of emitters and a photodiode in appropriate alignment to enable operation in either a transmissive mode or a reflectance mode. At least one predetermined wavelength of light is passed onto or through body tissues such as a finger, earlobe, or scalp, etc. and attenuation of light at that wavelength is detected. Likewise, the change in blood flow is determined by various techniques including optical, pressure, piezo and strain gage methods. Mathematical manipulation of the detected values compensates for the effects of body tissue and fluid and determines the hematocrit value. If an additional wavelength of light is used which attenuates light substantially differently by oxyhemoglobin and reduced hemoglobin, then the blood oxygen saturation value, independent of hematocrit may be determined. Further, if an additional wavelength of light is used which greatly attenuates light due to bilirubin (440 nm) or glucose (1060 nm), then the bilirubin or glucose value may also be determined. Also how to determine the hematocrit with a two step DC analysis technique is provided. Then a pulse wave is not required, so this method may be utilized in states of low blood pressure or low blood flow.

20 Claims, 15 Drawing Sheets

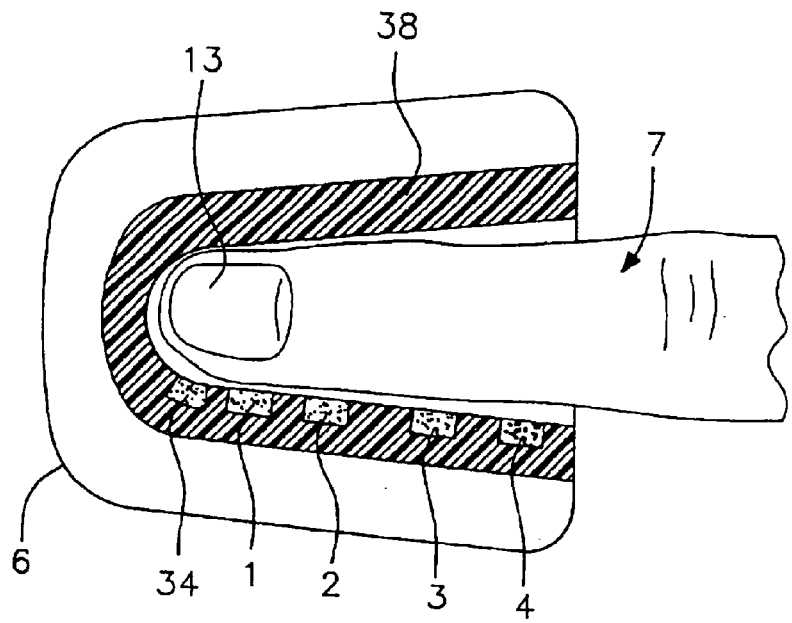
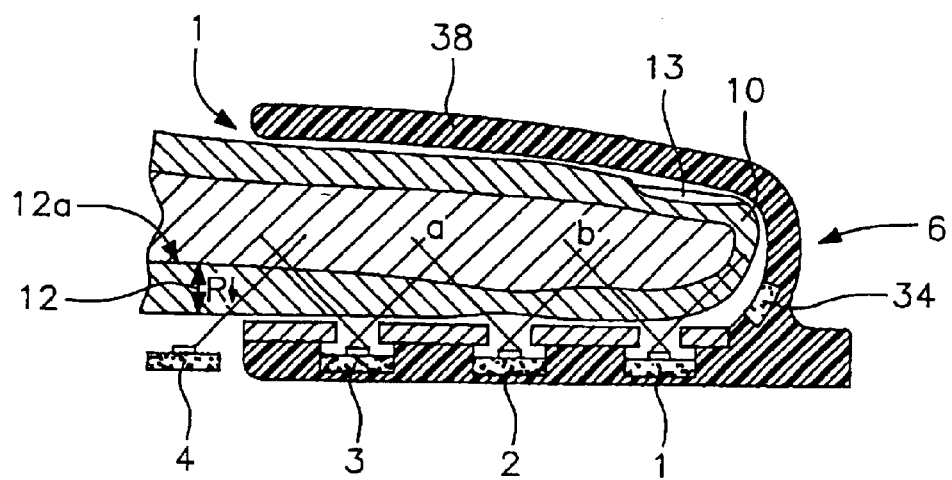

METHOD AND APPARATUS FOR NON-INVASIVE BLOOD CONSTITUENT MONITORING

CROSS-REFERENCE TO RELATED APPLICATIONS

This application is a continuation of U.S. application Ser. No. 09/771,596, filed Jan. 30, 2001, now U.S. Pat. No. 6,671,528 which is a continuation of U.S. application Ser. No. 09/244,756, filed Feb. 5, 1999, now U.S. Pat. No. 6,181,958, which is based on, and claims priority from U.S. Provisional Application Ser. No. 60/073,784, filed Feb. 5, 1998, all of which are incorporated herein by reference in their entireties.

BACKGROUND

1. The Field of Invention

The present invention relates to improvements in the systems and methods for non-invasively measuring one or more biologic constituent concentration values. More particularly, the present invention relates to non-invasive spectrophotometric systems and methods for quantitatively and continuously monitoring the hematocrit and other blood parameters.

2. The Prior Art

Modern medical practice utilizes a number of procedures and indicators to assess a patient's condition. One of these indicators is the patient's hematocrit. Hematocrit (often abbreviated as HCT) is the volume expressed as a percentage of the patient's blood which is occupied by red corpuscles, commonly referred to as red blood cells. The present invention is presented in the context of hematocrit. However, it is to be understood that the teachings of the present invention apply to any desired biologic constituent parameter.

Medical professionals routinely desire to know the hematocrit of a patient. In order to determine hematocrit using any of the techniques available to date, it is necessary to draw a sample of blood by puncturing a vein or invading a capillary. Then, using widely accepted techniques, the sample of blood is subjected to either high-speed centrifuge, cell counting, ultrasonic, conductometric or photometric methods of evaluating the sample of blood in a fixed container. Prior U.S. Pat. No. 5,372,136 indicates a system and methodology for determining the hematocrit non-invasively, without puncturing or invading the body, spectrophotometrically and continuously in a subject. The present invention relates to improvements upon the above cited system.

Beyond the above referenced patent, others have suggested various means of noninvasive measurement of hematocrit. Specifically, Mendelson, U.S. Pat. No. 5,277,181; Seeker, U.S. Pat. No. 5,188,108; Gonatas, U.S. Pat. No. 5,528,365; Ishikawa, U.S. Pat. No. 5,522,388; Shiga, U.S. Pat. No. 4,927,264; Tsuchiya, U.S. Pat. Nos. 5,441,054, 5,529,065, 5,517,987 and 5,477,051; and Chance, U.S. Pat. Nos. 5,353,799, 5,402,778, and 5,673,701 have attempted to define means of directly measuring desired biologic constituents such as hematocrit. Even though the various patents indicate the need to utilize multiple wavelengths measured at different detection sites and/or the need to perform differential or ratiometric operations on the detected optical signal, all fail to isolate and resolve the individual and specific scattering and absorption coefficients of the desired constituent. At best they address only bulk attenuation coefficients and/or bulk diffusion constants of the scattering media while attempting to resolve such constraints as tissue nonhomogeneity. As an example, tissue may be considered to contain a bulk absorptive coefficient due to blood, collagen, water, fibers, bone, fingernail, etc. Hence, in order to determine the absorptive coefficient of the blood itself, the bulk value of the tissue per se must be prorated by the amounts of the above constituents. Secondly, the actual absorptive coefficient of the blood must then be decoupled or isolated from its proration factor as well.

OBJECTS OF THE INVENTION

Thus, it is an object of the present invention to provide an improvement in the systems and methods for the non-invasive (transcutaneous) and continuous determination of the blood. Hematocrit in living tissue.

It is yet another object of the present invention to provide an improvement in the systems and methods for the non-invasive (transcutaneous) and continuous determination of the blood constituents, including glucose, bilirubin, cholesterol, tissue water, etc. in living tissue.

It is another object of the present invention to provide a system and method and apparatus for the display of both immediate and/or continuous visual information regarding the HCT of the subject.

It is yet another object of the present invention to provide a repeatable and reliable method and apparatus for the non-invasive determination of hematocrit transcutaneously and in real time even under varying physiological conditions.

Still another object of the present invention is to provide a method and apparatus for the instantaneous determination of the bulk absorption coefficient of the scattering media.

These and other objects and advantages of the invention will become more fully apparent from the description in the specification and claims, which follow.

SUMMARY OF THE INVENTION

In one aspect, the present invention accomplishes the transcutaneous, noninvasive, real-time and continuous measurement of the hematocrit and other blood constituents of the patient. That is, the electronic circuitry necessary is included to receive signals from a detector and to generate appropriate signals at various input sites as described in U.S. Pat. No. 5,372,136. Yet another aspect of the present invention is the ability to extract the blood absorption coefficient from the bulk tissue diffusion constant or the bulk absorption coefficient of the scattering media by requiring both physical and mathematical operations.

BRIEF DESCRIPTION OF THE DRAWINGS

FIGS. 1B and 1C are similar to FIG. 1A, but show the detector and emitter arrays operating in a reflectance mode.

DETAILED DESCRIPTION OF THE INVENTION

In a preferred embodiment of the invention, measurements are conducted using a modified version of the apparatus described in U.S. Pat. Nos. 5,456,253 and 5,372,136, both of which are incorporated herein as if reproduced in full below. Both of these patents form part of the present disclosure.

Thus, in a preferred embodiment, hematocrit is measured in living tissue located at some convenient location on the body, such as, an ear lobe, finger tip, nose or other accessible tissue sites. In a preferred embodiment the apparatus and signal manipulations described in U.S. Pat. No. 5,372,136 are utilized to measure various optical parameters that will be described hereafter. The numbered components in FIGS. 1, 1A, 1B, and 1C are similar to the numbers in FIG. 1 of U.S. Pat. No. 5,456,253.

Figure 1:
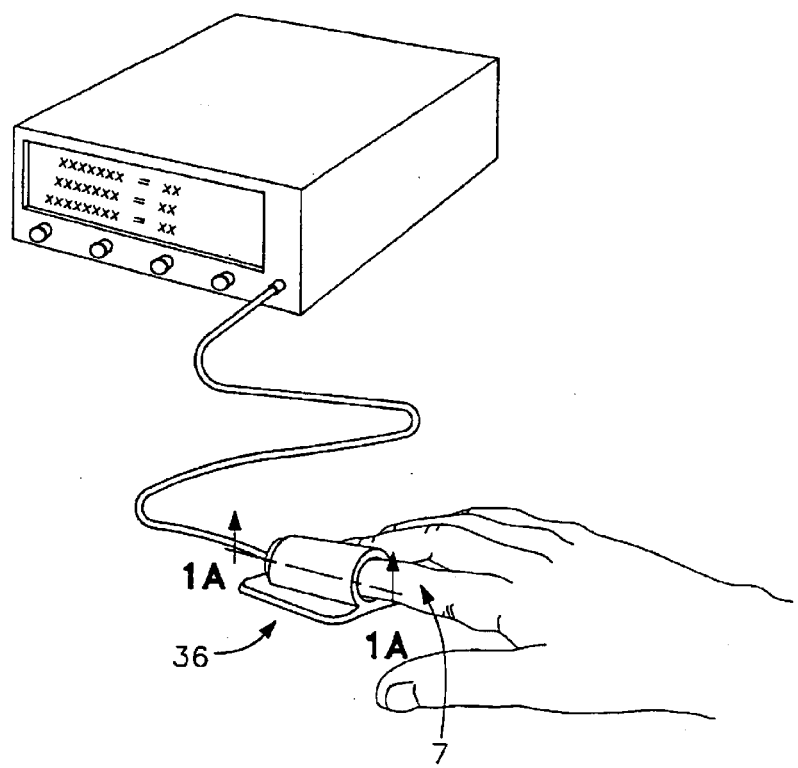
FIGS. 1 and 1A show a finger placed into a clam-shell type fixture constituting a receiving means for detector and emitter arrays operating in a transmission mode and the blood conduit which in the figures is the finger.

In the present disclosure, FIG. 1 shows the finger 7 of an individual placed into a clam-shell type fixture 6 wherein the optical and other physical measurements can be easily performed. The clam-shell type holder allows for adaptability to various finger sizes. However, other fixture methods such as FIGS. 1B through 1E, can be used to obtain similar physical data as using the clam-shell fixture.

Theoretical Basis of the Spectrophotometric and Mathematical Analysis for Transcutaneous Hematocrit Measurement Non-invasive, transcutaneous hematocrit measurement using a spectroscopic method is described below:

I. Introduction

Earlier spectrophotometric techniques have fallen short of being able to fully characterize the individual blood absorbance coefficients. The following discussion demonstrates the method of decoupling, or isolating from the bulk tissue attenuation parameters (including the convoluted absorptive and scattering parameters) the individual blood absorptive constants. This unique method identifies, isolates and compartmentalizes each of the contributing biologic elements of the tissue media. This decoupling process can either isolate the blood absorbance of interest and/or eliminate the scattering contribution from the bulk media measurement.

From photon diffusion analysis:

$$\frac{\partial^2}{\partial \rho^2}\Psi(\rho) - a^2\Psi(\rho) = \frac{-S(\rho)}{D} \quad (1)$$

where, $$D = \frac{1}{3(K+S)} \quad (2)$$

$$\alpha = \sqrt{3K(K+S)} \quad (3)$$

$$K = K_b X_b + K_s X_s + K_w X_w \quad (4)$$

$$K_b = \frac{H}{V}(\sigma_{ao}SAT + (1-SAT)\sigma_{ar}) + (1-H)K_p \quad (5)$$

$$S = S_b X_b + S_s X_s \quad (6)$$

$$S_b = \frac{\sigma_s H(1-H)(1.4-H)}{V} \quad (7)$$

and where, $\alpha$=Bulk attenuation coefficient of the tissue sample
K=Bulk absorption coefficient of the tissue sample
S=Bulk scattering coefficient of the tissue sample
D=Diffusion constant
$K_b$=Macroscopic absorption coefficient for whole blood (WB)
$S_b$=Macroscopic transport-corrected scattering coefficient for WB
$K_p$=Macroscopic absorption coefficient for plasma
$K_s$=Macroscopic absorption coefficient for skin, & other non water/blood components
$K_w$=Macroscopic absorption coefficient for water
V=Volume of a red blood cell (RBC)
H=Hematocrit, volume fraction of RBCs to total blood volume
SAT=Oxygen saturation %
$\sigma_{ao}$=Absorption cross-section of oxygenated RBCs
$\sigma_{ar}$=Absorption cross-section of deoxygenated RBCs
$\sigma_s$=Transport-corrected scattering cross-section of RBCs
$X_b$=Fractional volume of blood per total tissue volume
$X_s$=Fractional volume of skin, & non water/blood components per total tissue volume
$X_w$=Fractional volume of water per total tissue volume
$\Psi(\rho)$=The photon density at a distance $\rho$
$S(\rho)$=The source function.

II. Analysis

The light flux, or intensity, i, is given by $$i = D\frac{\partial \Psi}{\partial \rho}.$$

When evaluated at $\rho$=d, one solution to equation (1) is:

$$i = A\frac{e^{\alpha d}}{e^{2\alpha d} - 1} \quad (8)$$

where A is a nontrivial function of the tissue scattering coefficient, S, the distance, d (if small), and the bulk attenuation coefficient, $\alpha$. If $\alpha$ d>>1, then (8) becomes:

$$i = Ae^{-\alpha d} \quad (9)$$

where $$A \approx \frac{\alpha}{[d^n \cdot (1 - e^{-2\alpha d})]}$$

or $(1/d^2 + 1/\alpha d)$ for $0 < n < 2$,
where n is the power that d is raised to.

FIG. (2) shows the actual patient data plot of ln(i) vs. d, where $\alpha$ is determined directly from the slope of the line.

The attenuation coefficient, $\alpha$, is a bulk term which encompasses the attenuation measurement sensitivity to variations in skin color, presence of bone, callous, blood and water content, etc. In addition, $\alpha$ expresses the optical "path lengthening" effects of both the absorption and scattering characteristics of the tissue. Therefore, since $\alpha$ is a function of HCT and the intensity of the transmitted light can be measured, the HCT can be calculated by manipulation of the preceding relationships.

Beginning with equation (9), the troublesome and complex tissue function, A, can be eliminated by taking the logarithm of (9) and differentiating with respect to the distance, d. Unfortunately the term $X_b$ is not known but changes with time as a result of a patient's cardiac cycle. Therefore, by differentiating with respect to time, this parameter becomes the time rate of change of blood volume which can be obtained through several methods described below. These time and distance derivatives may be performed in either order.

[1] Taking the logarithm of (9) and differentiating with respect to the distance, d, yields:

$$\alpha = \frac{\partial [\ln(i)]}{\partial d} \tag{10}$$

Next the derivative of (10) with respect to time, t, gives:

$$\frac{\partial \alpha}{\partial t} = \frac{\partial \left( \frac{\partial [\ln(i)]}{\partial d} \right)}{\partial t} \tag{11}$$

[2] Alternatively, first differentiate (9) with respect to time, t, to get:

$$\frac{\partial i}{\partial t} = \frac{\partial i}{\partial X_b} \frac{\partial X_b}{\partial t} + \frac{\partial i}{\partial X_s} \frac{\partial X_s}{\partial t} + \frac{\partial i}{\partial X_w} \frac{\partial X_w}{\partial t} \tag{12}$$

When $$\frac{\partial i}{\partial X_s} \frac{\partial X_s}{\partial t} \text{ and } \frac{\partial i}{\partial X_w} \frac{\partial X_w}{\partial t}$$

are negligible, and normalizing (12) by i yields:

$$\frac{\partial i / \partial t}{i} = \frac{\partial X_b}{\partial t} \left( \frac{\partial \alpha}{\partial X_b} d - \frac{1}{A} \frac{\partial A}{\partial X_b} \right) \text{ or,} \tag{13}$$

$$\frac{\partial i / \partial t}{i} = \frac{\partial \alpha}{\partial t} (d - d_o), \text{ where } d_o \approx \frac{1}{a} - \frac{2d}{e^{2\alpha d} - 1} \tag{13a}$$

Figure 3:
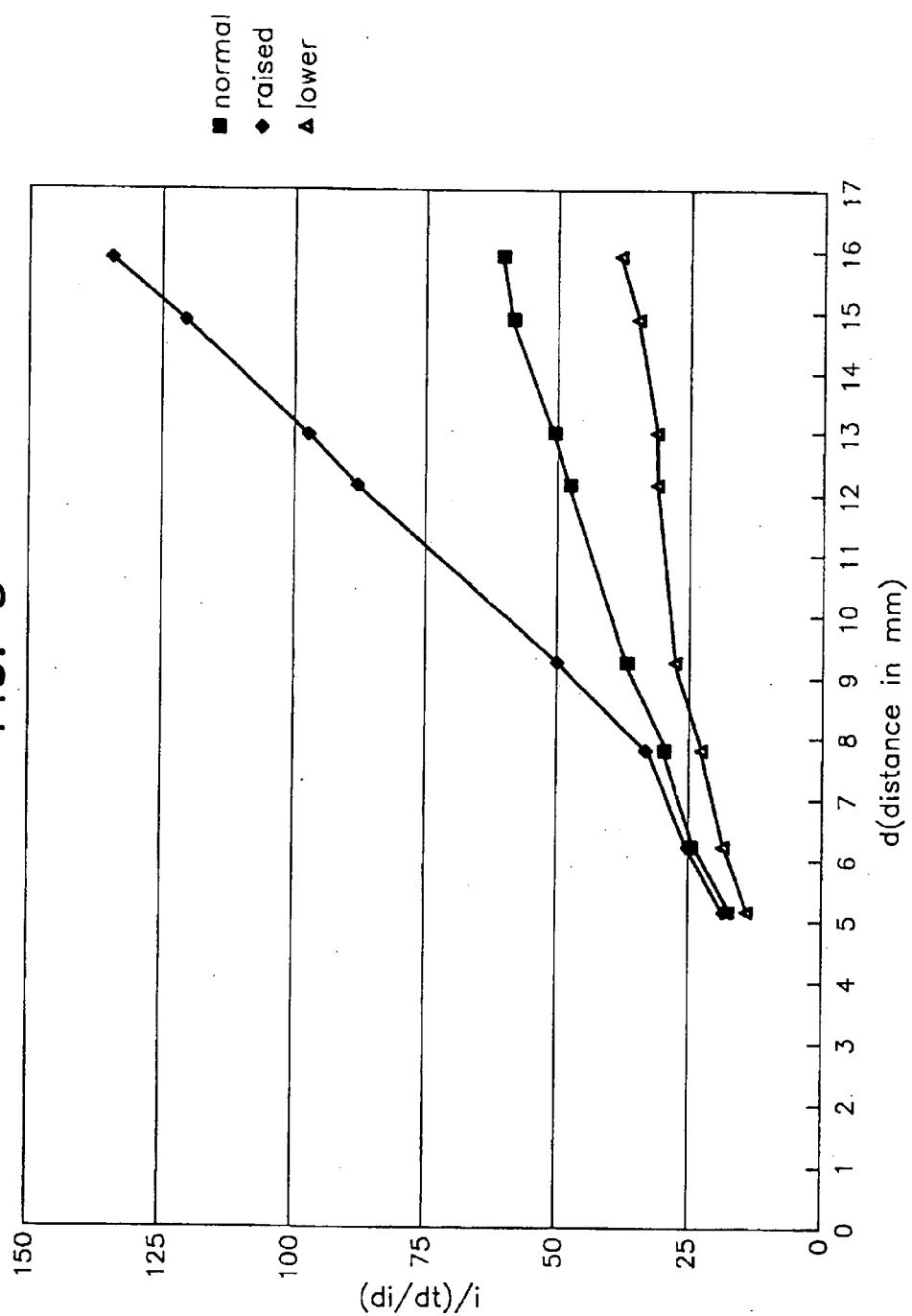
FIG. 3 illustrates actual patient data of the $(\partial i/\partial t)/i$ dependence on d.

FIG. 3 plainly demonstrates the offset term when the various graph lines are extrapolated to d=0. The amount of offset is shown along the y-axis.

Next differentiate (13) with respect to distance, d, to eliminate that offset term to get:

$$\frac{\partial \left( \frac{\partial i / \partial t}{i} \right)}{\partial d} = \frac{\partial X_b}{\partial t} \left( \frac{\partial \alpha}{\partial X_b} \right) = \frac{\partial \alpha}{\partial t} \tag{14}$$

Equations (3)–(7) are now used to extract the hematocrit from $\alpha$. Squaring (3) and differentiating with respect to time results in:

$$2\alpha \frac{\partial \alpha}{\partial t} = 3 \left[ \frac{\partial K}{\partial t} (2K + S) + K \frac{\partial S}{\partial t} \right] \tag{15}$$

Substituting the derivatives of (4) and (6) into (15) and rearranging:

$$\frac{\partial \alpha}{\partial t} = \tag{16}$$

$$\frac{3}{2\alpha} \left[ \left( \frac{\partial X_b}{\partial t} K_b + \frac{\partial X_s}{\partial t} K_s + \frac{\partial X_w}{\partial t} K_w \right) (2K + S) + K \left( \frac{\partial X_b}{\partial t} S_b + \frac{\partial X_s}{\partial t} S_s \right) \right]$$

At 805 nm, $$\frac{\partial X_b}{\partial t} K_b \gg \frac{\partial X_s}{\partial t} K_s, \frac{\partial X_b}{\partial t} K_b \gg \frac{\partial X_w}{\partial t} K_w, \frac{\partial X_b}{\partial t} S_b \gg \frac{\partial X_s}{\partial t} S_s$$

and K<<S so that (16) can be simplified to:

$$\frac{\partial \alpha}{\partial t} = \frac{3}{2\alpha} \frac{\partial X_b}{\partial t} (K_b S + K S_b) \tag{17}$$

By using the 805 nm wavelength the red blood cell absorption cross-section constants are equal, $\sigma_{ao} = \sigma_{ar}$, and $K_p$ is negligible. The hematocrit can then be determined directly from $K_b$ as (5) simplifies to:

$$H = \frac{V}{\sigma_a} K_b \tag{17a}$$

Figure 4:
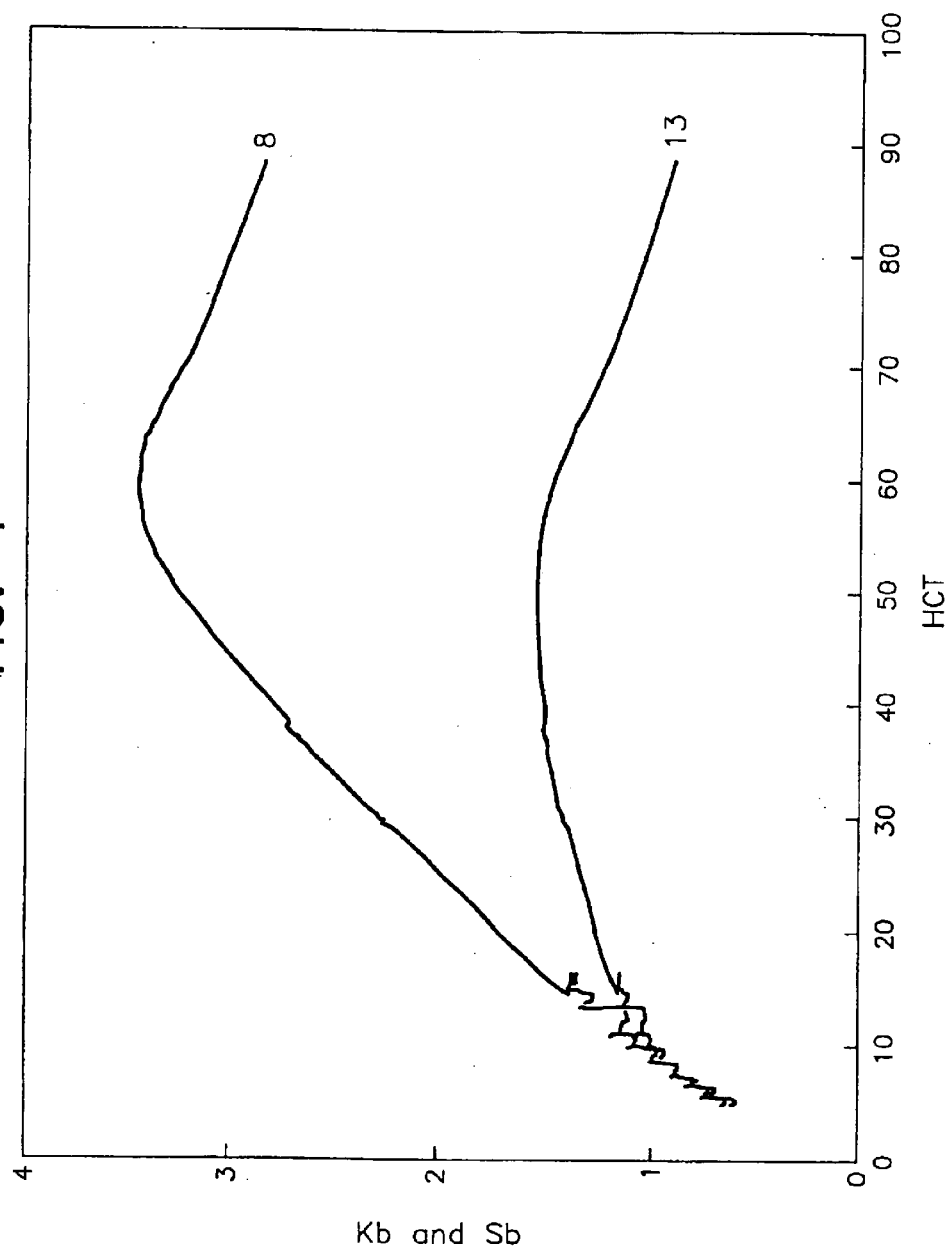
FIG. 4 shows the blood absorption coefficient's dependence on hematocrit.

FIG. 4 shows the linearity of $K_b(H)$.

If $K_b S \gg K S_b$, where S is approximately 1.0/mm in human tissue, then solving (17) for $K_b$ and substituting into (17a) gives:

$$H = \frac{\frac{2V}{3\sigma_a} \alpha \frac{\partial \alpha}{\partial t}}{\frac{\partial X_b}{\partial t} S} \tag{18}$$

To rewrite in terms of measurable intensity, i, (10) and (14) are substituted into (18) to obtain:

$$H = \frac{\frac{2V}{3\sigma_a} \frac{\partial [\ln(i)]}{\partial d} \frac{\partial [(\partial i / \partial t) / i]}{\partial d}}{\frac{\partial X_b}{\partial t} S} \tag{19}$$

If $K_b S$ is not $\gg K S_b$, then substituting (5) and (7) into (17a) and rearranging terms yields:

$$H = \frac{2\alpha}{3} \frac{\partial \alpha}{\partial t} \bigg/ \frac{\partial X_b}{\partial t} \left[ S\frac{\sigma_a}{V} + K\frac{\sigma_s}{V}(1-H)(1.4-H) \right] \quad (18a)$$

Alternatively from (13a):

$$H \approx \frac{\alpha \cdot (\partial i / \partial t / i)}{(d - d_o) \cdot X_b'} \quad (18b)$$

Equation (18a) indicates a small nonlinearity in H may occur based on the magnitude of K for a given individual.

It should be reiterated that the change in received intensity with time is a result of the change in normalized blood volume resulting from the cardiac cycle itself as blood pulses through the examined tissue. As the intensity of the received light is measured, its time rate of change can be calculated. The change with distance can be determined by placing multiple emitters (such as 1–4 in FIG. 1A) and/or multiple detectors such that multiple thicknesses of tissue and hence, lengths of tissue are penetrated.

To examine $$\frac{\partial X_b}{\partial t}$$

further, the following can be defined for the illuminated tissue:
$V_b$=Volume of blood,
$V_w$=Volume of water, and
$V_s$=Volume of skin, tissue and other non-water or blood components.
By definition, $$X_b = \frac{V_b}{V_b + V_w + V_s} \quad (20)$$

differentiating (20) with respect to time gives:

$$\frac{\partial X_b}{\partial t} = \frac{(V_w + V_s)\frac{\partial V_b}{\partial t} - V_b \frac{\partial V_w}{\partial t}}{(V_b + V_w + V_s)^2} \quad (21)$$

Since $$\frac{\partial V_w}{\partial t} \ll \frac{\partial V_b}{\partial t}$$

and $V_b \ll V_w+V_s$, (21) simplifies to:

$$\frac{\partial X_b}{\partial t} = \frac{\frac{\partial V_b}{\partial t}}{V_{total}} \quad (22)$$

It is emphasized that $\alpha$ is a function of the bulk absorption and scattering coefficients, K and S, as well as hematocrit, H. Further, that K and S are functions of the fractional volumes of each constituent, $X_b$, $X_s$, and $X_w$, which must be used to prorate the individual absorption and scattering coefficients, $K_b$, $K_s$, $K_w$, $S_b$ and $S_s$. Therefore, the transducer system must be responsive not only to a change in volume ($\Delta V$) due to the influx of the blood, but must also be responsive to the normalized change in volume of blood, normalized to the total volume of the finger ($V_f$)or tissue being measured, $$\left( \frac{\Delta V_f}{V_f} \right).$$

For Reflectance (R) measurements in homogenous tissue:

$R=Ae^{-\alpha r}$, where $A\approx(1/r^2+1/\alpha r)$, where r is the radial distance, and $$\frac{dR}{R} = \alpha'(r/(\alpha^2 + \alpha r))$$

Figure 1A:
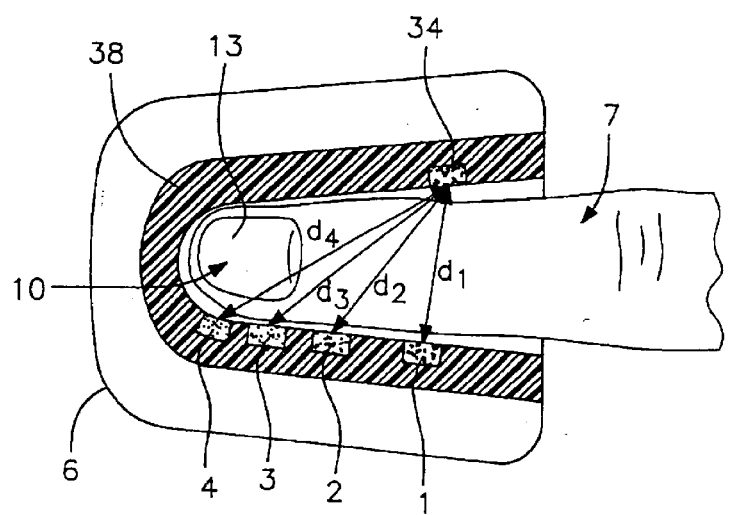
Figure 1D:
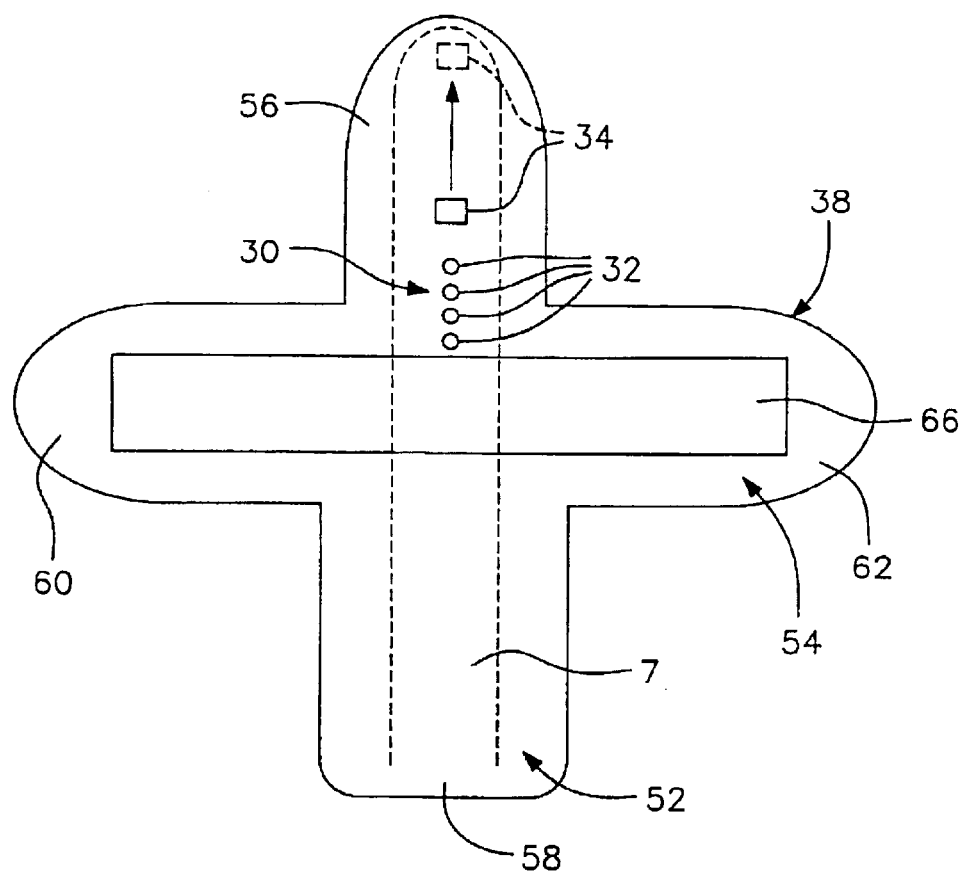
FIG. 1D is a schematic diagram for a mylar base with a detector, emitters and either a strain gage or a pressure transducer for inclusion in the clam-shell fixture.
Figure 1E:
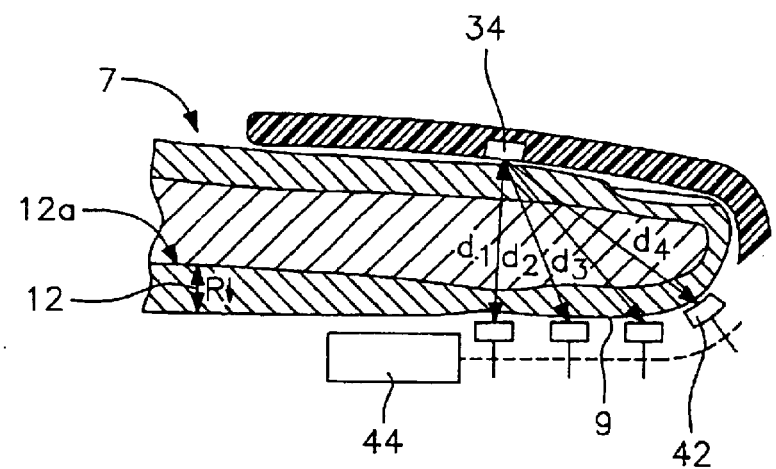
FIG. 1E is a schematic diagram for a detector emitter array using a single, moveable emitter in a transmission mode.
Figure 2:
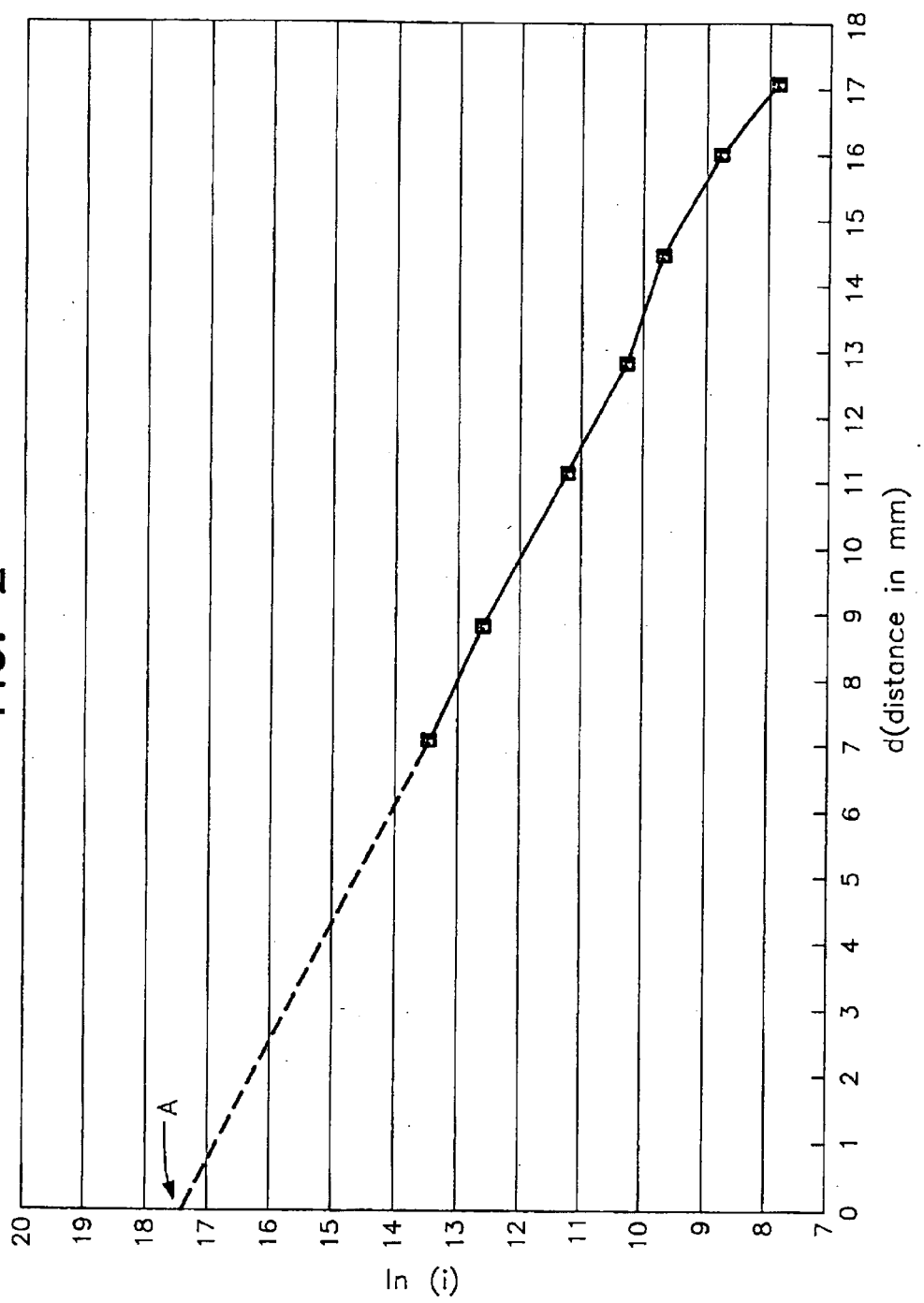
FIG. 2 shows actual patient data plot of ln(i) vs. d.

However, for tissue, which is typically non-homogeneous with a dermal and subcutaneous layer, the reflectance will not be a trivial function but can be described as approximately:

$$R=[(C_1+C_2)\exp(-C_3 \cdot r)]/r^n$$

Where $C_1$ and $C_2$ are inter-related photon flux densities between the dermal layer 12 and the subcutaneous layer, 12a (see FIGS. 1C and 1E). Likewise, $C_3$ is a strong function of $z_1$, $z_2$, $\alpha_1$, and $\alpha_2$; i.e., the thickness of the dermis or dermal layer 12, subcutaneous layer 12a, and their respective $\alpha$'s.

Since $C_3'$ is a function of the inter-related photon flux densities $C_1$ and/or $C_2$ and if $Xb'_1$ does not equal $Xb'_2$, then the slope $C_3'$ will not be nulled out by the Xb' monitors mentioned. Therefore, $Xb_2'$ must be greater than $Xb_1'$. Then the pressure or piezo monitors will compensate correctly. The circular pressure balloon is ideal for not only sensing the change in a pressure, but also providing a pressure against the dermis causing $Xb_1'$ to be small. However, recognizing that the penetration depth of the 800 nm light typically extends through dermal layer 12 into the deep tissue, subcutaneous layer 12a, a different wavelength selection is appropriate. Thusly, when the photons only penetrate into the dermal layer 12, $C_3'$ will only be a function of $z_1$ and $\alpha_1$. Those selected wavelengths, as mentioned in U.S. Pat. No. 5,372,136, would be the green (570–595 nm) wavelength and 1300 nm wavelength. The green wavelengths are used as the hematocrit bearing wavelength and the 1300 nm wavelength is used as the non-hematocrit bearing, or reference wavelength. That is, for reflectance measurements the green (Gr)-1300 wavelength pair would give the hematocrit information as:

$$\frac{\Delta Gr/Gr}{\Delta 1300/1300} \cdot \frac{\alpha_{Gr}}{\alpha_{1300}} = f(HCT)$$

III. Methods of $$\frac{\partial X_b}{\partial t}$$

Measurement $\partial X_b/\partial t$ can be measured and compensated for through the use of a number of different methods—(a) a pressure transducer, (b) a strain transducer such as piezo electric film or strain gage, (e) a different wavelength of light, such as 1300 nm, which also holds $\partial X_b/\partial t$ information, but holds little hematocrit information, or (d) other transducers. The individual methods of obtaining $\partial X_b/\partial t$ are addressed below.

A. Pressure Transducer Measurement of $$\frac{\partial X_b}{\partial t}$$

Consider a pressure transducer system 36 with a gas filled bladder 38 surrounding a finger tip 10 of a patient contained within a fixed volume clam shell fixture 6, see FIGS. 1, 1A–1D. The same derivations, equations, and results would apply to any other body appendage or tissue that could be contacted such that a change in the tissue volume would change the pressure of the contacted pressure transducer system. For a finger note:

$$V_{clam} = V_{sys} + V_f \quad (23)$$

where
$V_{clam}$=Clam-shell fixture volume
$V_{sys}$=Bladder system volume
$V_f$=Finger volume Also $\Delta V_f = -\Delta V_{sys}$. The system will have a bulk modulus of elasticity, $\beta$, such that:

$$\frac{\Delta V_{sys}}{V_{sys}} = \frac{-\Delta P_{sys-}}{\beta} = \frac{-\Delta V_f}{V_{sys}} \quad (24)$$

Substituting (23) into (24) results in:

$$\frac{\Delta V_f}{V_f} = \left(\frac{V_{clam}}{V_f} - 1\right)\frac{\Delta P_{sys}}{\beta} \quad (25)$$

Since $\Delta V_f = \Delta V_b$ then from (25) we have:

$$\frac{\partial X_b}{\partial t} = \left(\frac{V_{clam}}{V_f} - 1\right)\frac{\Delta P_{sys}}{\beta} \quad (25a)$$

Figure 5:
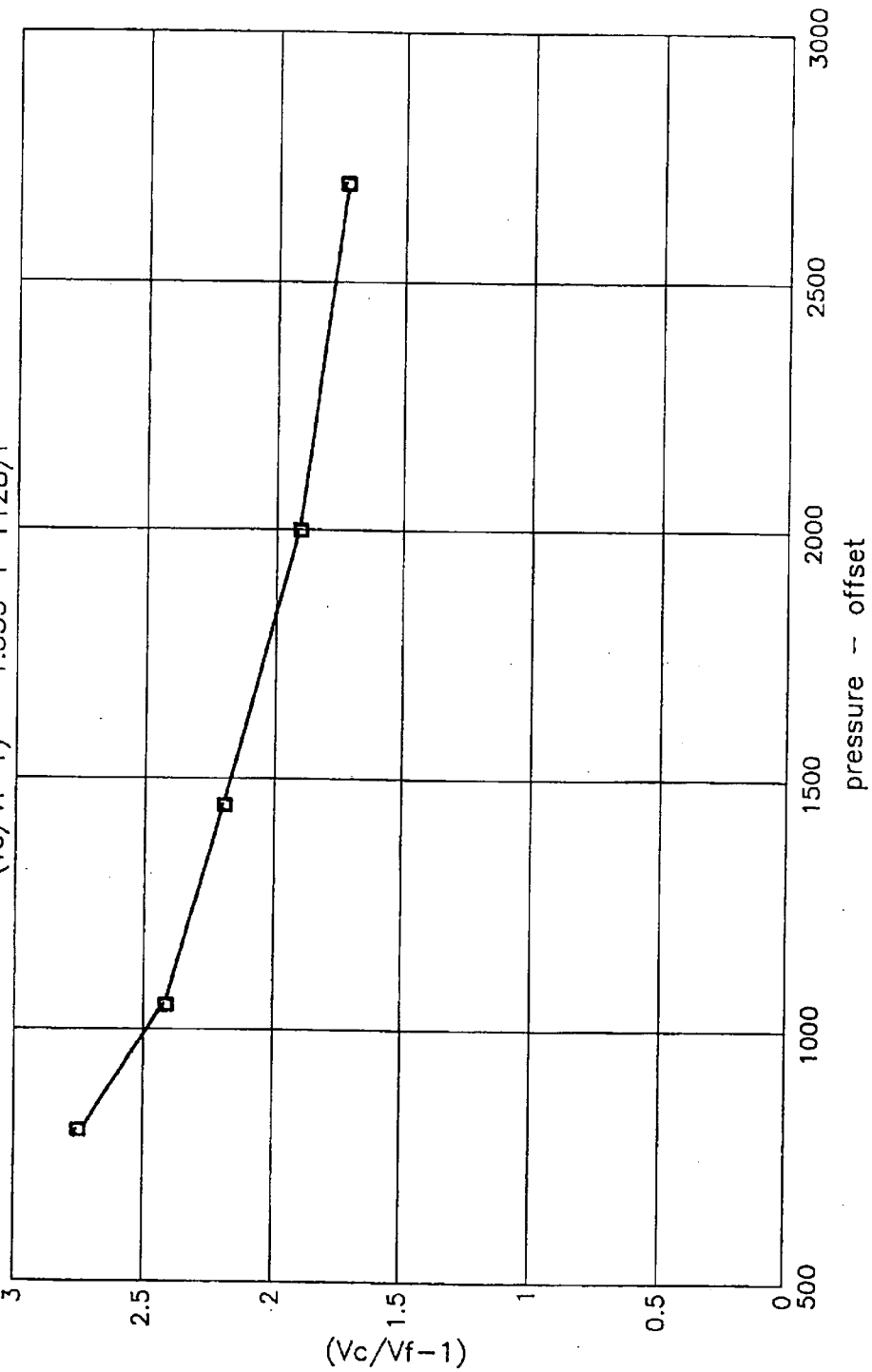
FIG. 5 indicates the nonlinear relationship between the $V_c/V_f$ and pressure.

As stated above, $\beta$ is a constant of the pressure transducer system. However, an empirical solution for $$\left(\frac{V_{clam}}{V_f} - 1\right)$$

was found to have a nonlinear relation to the pressure of the transducer system. For a given clam shell—pressure transducer embodiment a polynomial, F(p), can accurately describe $$\left(\frac{V_{clam}}{V_f} - 1\right),$$

see FIG. 5

B. Strain Transducer (Strain Gage/Piezo Electric Film) Measurement of $$\frac{\partial X_b}{\partial t}$$

Again it is assumed that $\Delta V_b = \Delta V_f$, and that the finger changes volume only by a change in diameter. A strain gage or piezo electric film is secured tightly around the finger (again any applicable body appendage or tissue would apply) such that a change in diameter would produce a strain in the transducer. Specifically assuming a cylindrical finger:

$$\frac{\partial V_b}{\partial t} = \frac{\partial V_f}{\partial t} = \frac{\partial(\pi z r^2)}{\partial t} = 2\pi z r \frac{\partial r}{\partial t} \quad (26)$$

Normalizing with respect to $V_f$, yields:

$$\frac{\partial X_b}{\partial t} = -\frac{\frac{\partial V_b}{\partial t}}{V_{total}} = \frac{2\pi z r \frac{\partial r}{\partial t}}{\pi z r^2} = \frac{2}{r}\frac{\partial r}{\partial t} \quad (27)$$

A change in the length of the transducer element is related to a change in finger radius by $\Delta L = 2\pi \Delta r$, therefore:

$$\frac{\partial X_b}{\partial t} = \frac{2\left(\frac{\partial L}{\partial t}\right)}{L_t} = 2\gamma(t) \quad (28)$$

where $$\gamma(t) = \frac{\frac{\partial L}{\partial t}}{L}$$

at is the rate of change in the strain as a function of time. For a strain gage this value can be measured from an appropriate electrical circuit, see FIG. 6, as it is proportional to the rate of change in the gage resistance.

For a piezo electric film the voltage produced is proportional to the strain, therefore:

$$\frac{\partial Xb}{\partial t} = \frac{2}{g_{31}\tau}\frac{\partial v(t)}{\partial t} \quad (29)$$

where, $g_{31}$ is the piezoelectric coefficient for the stretch axis, $\tau$ is the film thickness and $v(t)$ is the open-circuit output voltage.

C. 1300 nm Light Measurement of $$\frac{\partial X_b}{\partial t}$$

The selection of the 1300 nm wavelength is based on criteria established in U.S. Pat. No. 5,372,136. The approach here is not to solve for $\partial X_b/\partial_t$ and substitute into (19) but to ratiometrically eliminate $\partial X_b/\partial t$. In the case of the 1300 nm reference wavelength, the assumptions following equation (12) are no longer valid; i.e., $\partial X_s/\partial t$ and $\partial X_w/\partial t$ are not negligible, since water absorption at 1300 nm is so large. Hence, for the 1300 nm equations (13), (14) and (15) would result in:

$$\left(\frac{\partial \alpha}{\partial t}\right)_{13} = \frac{3}{2\alpha}\left[\{(2K+S)K_b + KS_b\}\frac{\partial X_b}{\partial t} + \{(2K+S)K_s + KS_s\}\frac{\partial X_s}{\partial t} + \{(2K+S)K_w\}\frac{\partial X_w}{\partial t}\right] \quad (30)$$

where, $\alpha$, and the bulk and material specific K, and S are wavelength ($\lambda$) dependent. Recalling that, $X_b + X_s + X_w = 1$, by definition, and that:

$$-\frac{\partial X_b}{\partial t} - \frac{\partial X_s}{\partial t} = \frac{\partial X_w}{\partial t} \quad (31)$$

By substituting (31) into (30) and noting that $K_{w13}=K_{b13}$, the following is obtained:

$$\left(\frac{\partial \alpha}{\partial t}\right)_{13} = \frac{3}{2\alpha}\left[\{KS_b\}\frac{\partial X_b}{\partial t} + \{(2K+S)[K_s - K_w] + K_sS_s\}\frac{\partial X_s}{\partial t}\right] \quad (32)$$

Since, $$\frac{\partial X_b}{\partial t} >> \frac{\partial X_s}{\partial t}, \quad (32)$$

becomes:

$$\left(\frac{\partial \alpha}{\partial t}\right)_{13} = \frac{3}{2\alpha_{13}}\{KS_b\}_{13}\frac{\partial X_b}{\partial t} \quad (33)$$

Therefore, to eliminate $$\frac{\partial Xb}{\partial t}$$

and solve for the hematocrit, (17) is divided by (33) yielding:

$$\frac{(\partial \alpha / \partial t)_g}{(\partial \alpha / \partial t)_{13}} = \frac{\alpha_{13}}{\alpha_g}\frac{K_{b_g}S_g}{K_{13}S_{b_{13}}} \quad (34)$$

Figure 7:
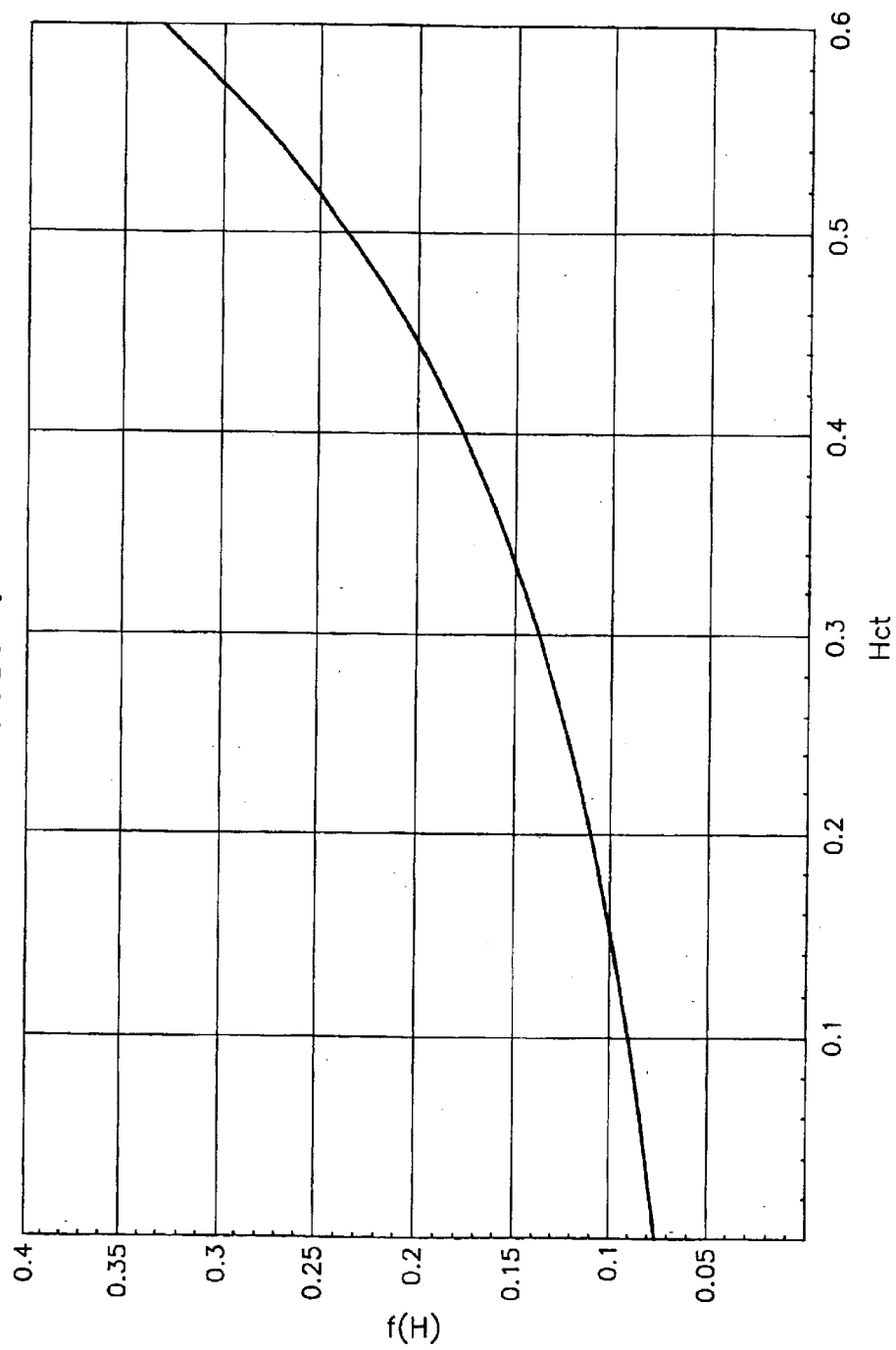
FIG. 7 is the plot of f(H) vs. measured Hematocrit.

Since $S_g$ and $K_{13}$ are well behaved and known (let $K_{13}/S_g=G$) in human tissue and the ratio $$\frac{K_{b_g}}{S_{b_{13}}}$$

is a function of H, then rearranging (34) gives:

$$f(H) = \frac{K_{b_g}}{S_{b_{13}}} = \frac{\alpha_8}{\alpha_{13}}\frac{\left(\frac{\partial \alpha}{\partial t}\right)_8}{\left(\frac{\partial \alpha}{\partial t}\right)_{13}}G \quad (35)$$

Where $$\frac{\partial \alpha}{\partial t}$$

can be measured using (11) or (14). See FIG. 7 for f(H).
D. Other $\partial X_b/\partial t$ measurements such as doppler, ultrasonic, electrical conductivity, magnetic permeability and other techniques have similar derivations. The important consideration is that $\partial X_b/\partial t$ is a normalized time varying quantity.

IV. Analytical Implementation

If hematocrit is constant over a given time interval, averaging can eliminate system noise whose frequency components have corresponding periods much shorter than the interval. In addition, by observing the data variance during the interval it may be determined that the data is invalid. In the present system, the data acquisition rate is approximately 1000 data samples per second. This means that within a typical human pulse about 1000 samples of data are available for appropriate numerical analysis, averaging and qualification. Recognizing that both the intensity of light and the pressure in the transducer system are changing in time during the influx of blood is of great importance. Since the parametric relationship of $\partial \alpha/\partial t$ as a function of $\partial P/\partial t$ (where P is pressure) during the cardiac cycle should be linear, a multiplicity of data points facilitate qualification of the signal for accuracy and linearity. Whereas, prior techniques involving only the peak and valley values of the cardiac cycle require numerous pulses to qualify the data set. See FIGS. 8, 9 and 10.

Figure 8:
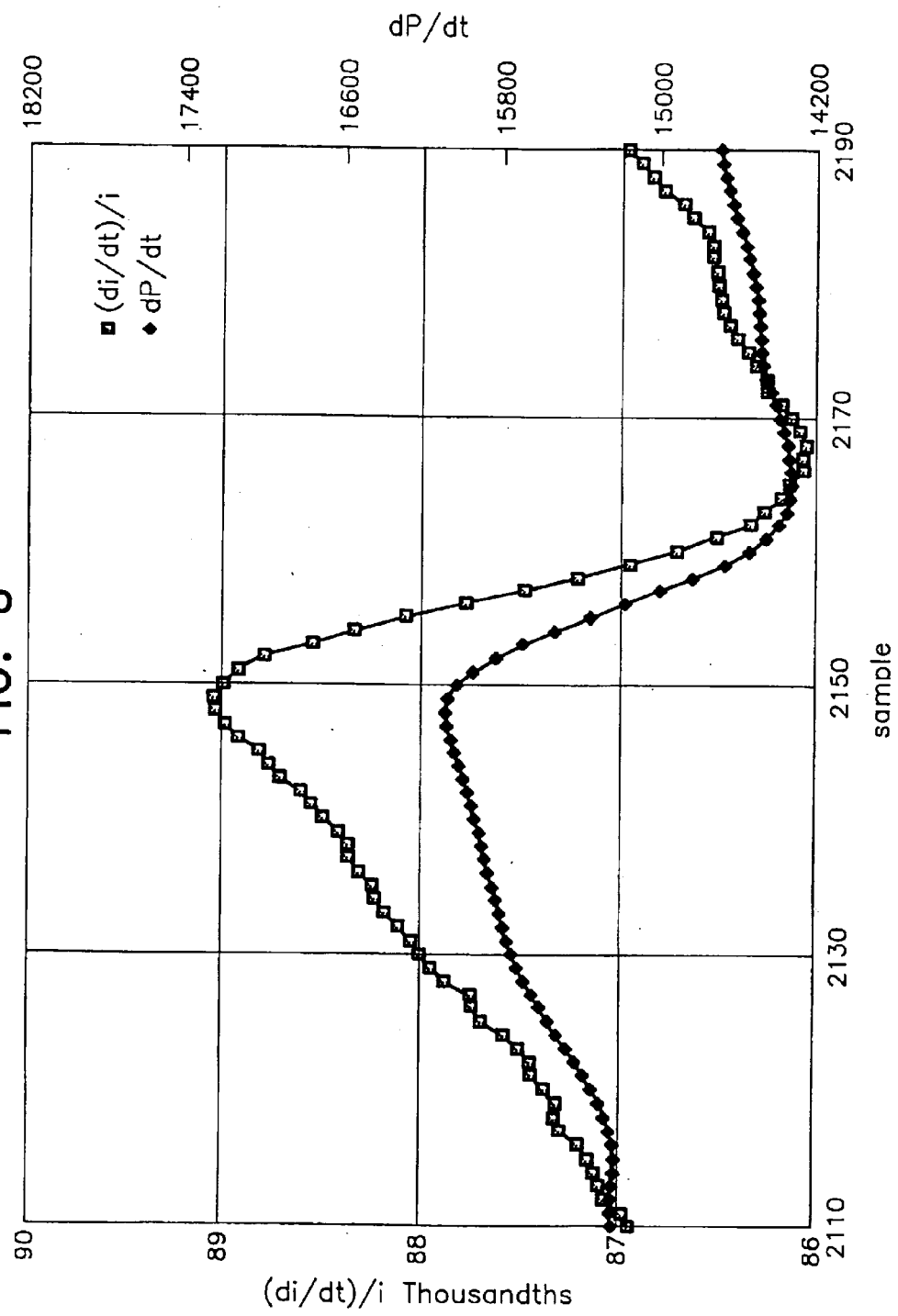
FIG. 8 shows the instantaneous time derivatives of $(\partial i/\partial t)/i$ and $\partial P/\partial t$ versus time during one cardiac pulse.

FIG. 8 shows di/dt/i as well as dP/dt verses time during the cardiac pulse—it is a pulse showing ≈200+ data samples during the pulse.

Figure 9:
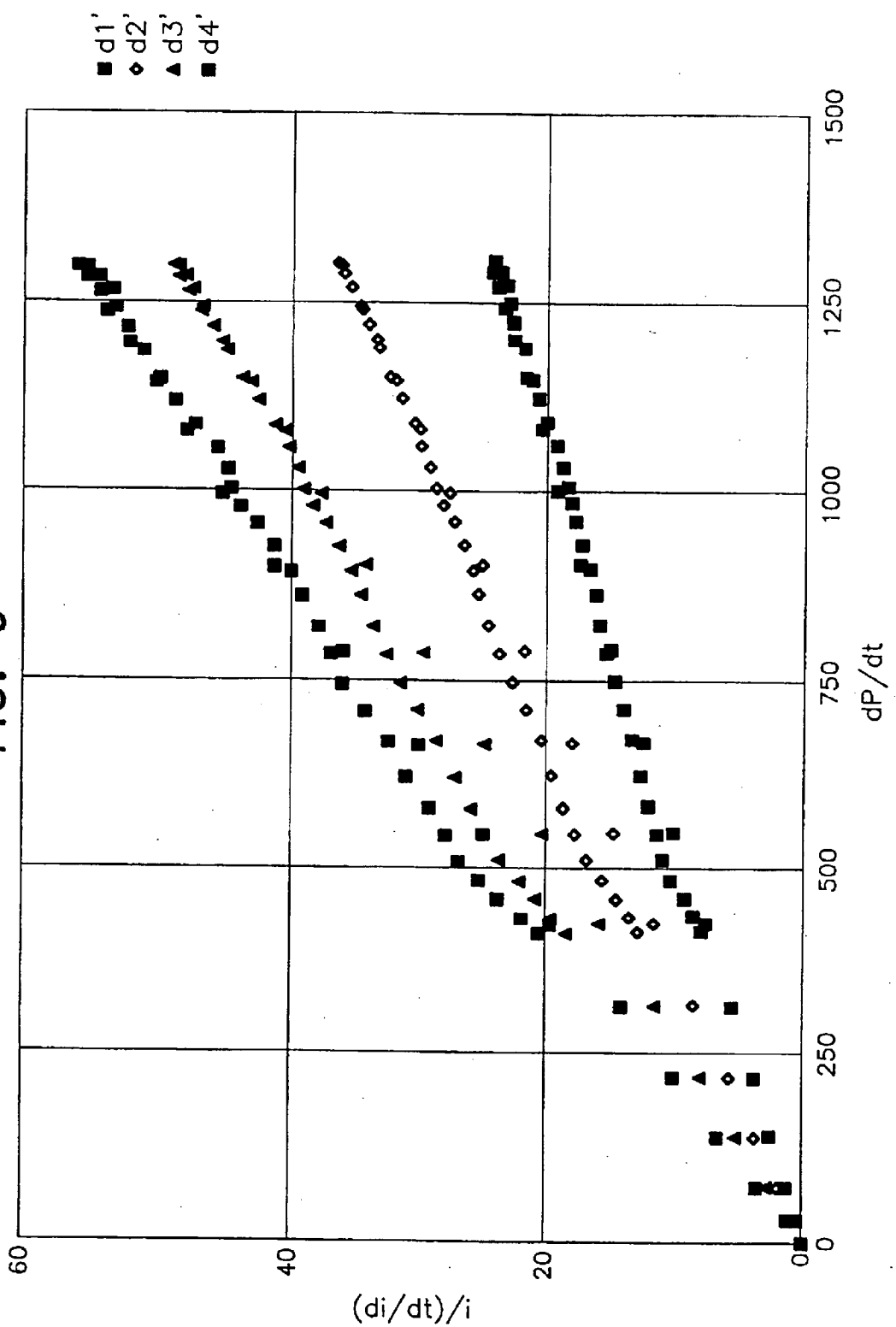
FIG. 9 plots $(\partial i/\partial t)/i$ versus $\partial P/\partial t$ for a given human pulse at $d_1$, $d_2$, $d_3$, and $d_4$ FIG. 10 plots $(\partial i/\partial t)/(\partial P/\partial t)$ versus time during a single cardiac pulse cycle.

FIG. 9 shows (di/dt)/i vs dP/dt showing that within one cardiac pulse 200 plus data samples are linearly related, i.e. trace up out of the "0" origin up to a maximum value and then back down toward the origin again.

Figure 10:
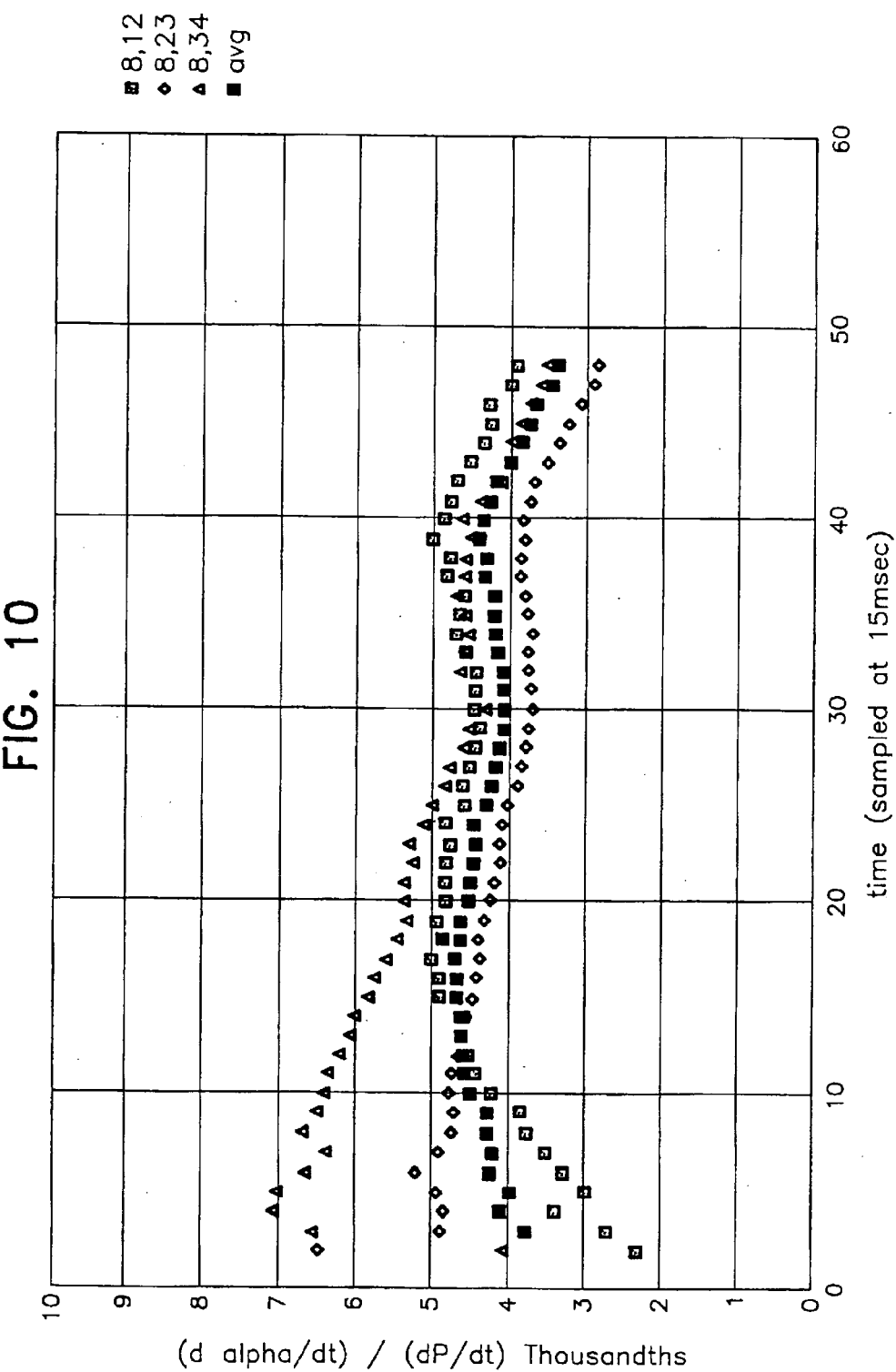

FIG. 10 shows dα/dt/dP/dt versus time during one single cardiac pulse with 200 plus samples of data from time 15–45 giving a value of about 4.5 thousandths. The data can then be averaged, as if 200+ individuals pulse (max-min) values were actually taken as present day oxymeters do.

A. Homogeneity

Since the above derivations are based on the assumption of tissue homogeneity (i.e., $\partial X_{b1}/\partial t=\partial X_{b2}/\partial t$, $A_1=A_2$, $\partial A_1/\partial X_b=\partial A_2/\partial X_b$, $\alpha_1=\alpha_2$, etc.), high-speed, single-pulse, multiple parameter sampling allows for mathematical qualification of homogeneity, by requiring linearity of ln(i) vs. d and $(\partial i/\partial t)/i$ vs. d. Under these constraints and when qualified as homogeneous, $(\partial \alpha/\partial t)/(\partial P/\partial t)$ also may be assumed to be linear over the entire pulse contour. Finally, both $\alpha$ and $\partial \alpha/\partial t$ must also be linear, further assuring homogeneity in $X_b$, and in $\partial X_b/\partial t$.

B. Circuitry

See U.S. Pat. No. 5,372,136 for the operational circuitry description, which allows for high speed sampling of the optical intensities. See FIGS. 6 and 10 for similar circuitry considerations for sampling of pressure, peizo, and strain-gage measurements.

Figure 6:
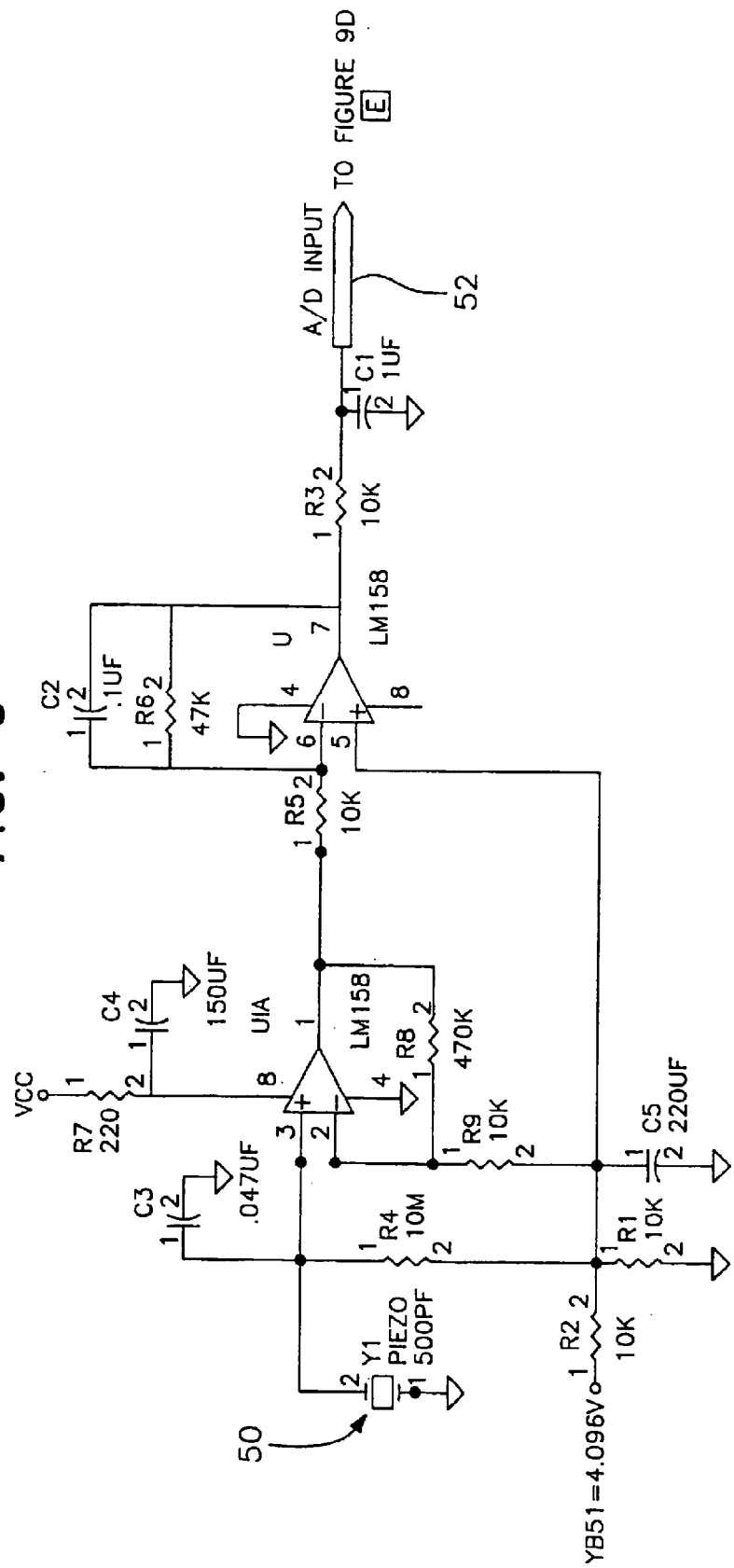
FIG. 6 shows the electrical circuit diagram of the piezo film/strain gage transducer means.
Figure 11:
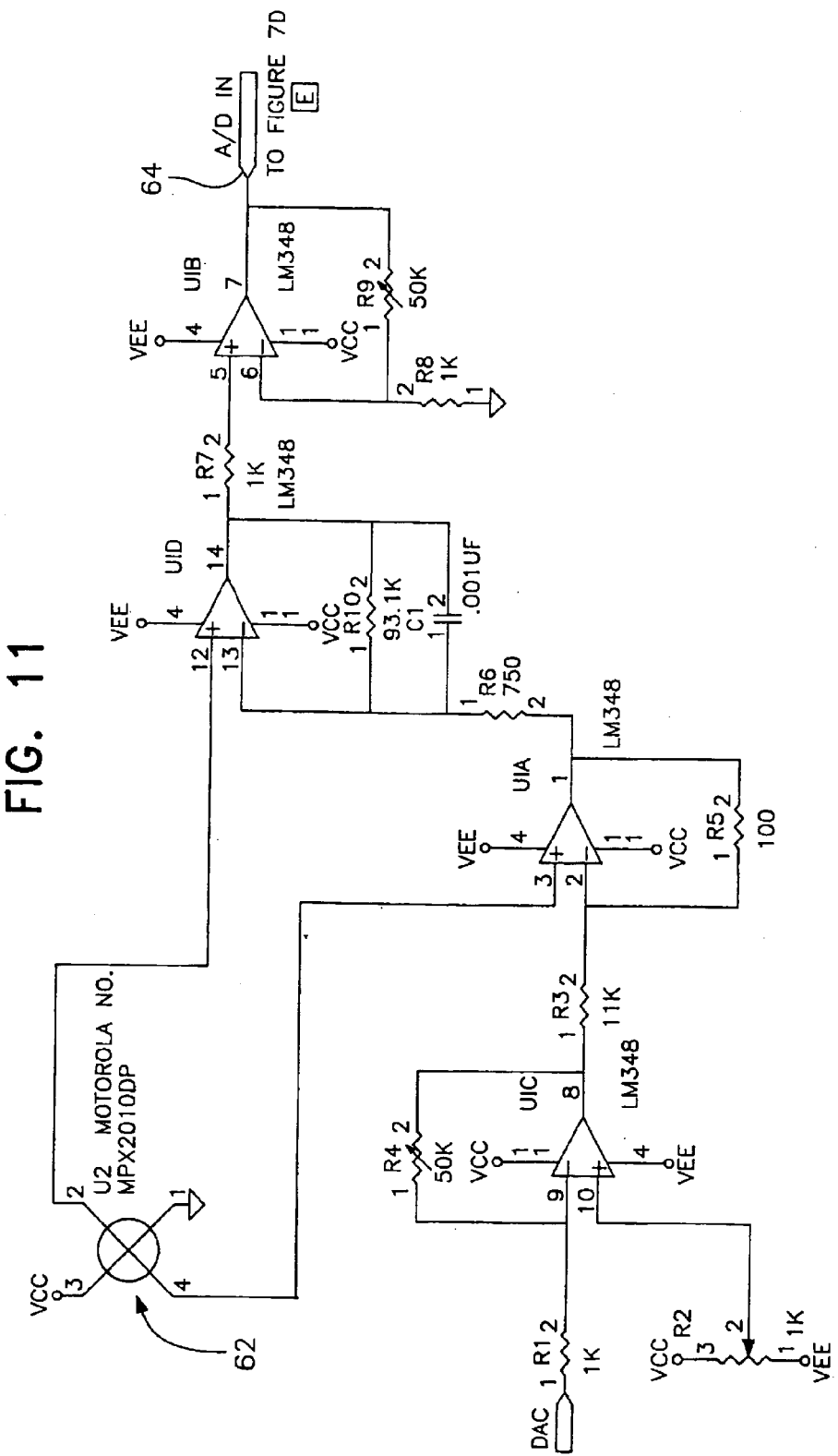
FIG. 11 is the circuit diagram of the pressure transducer means.

The circuitry shown and discussed in U.S. Pat. No. 5,372,136 is programmable by conventional techniques to solve and implement the equations and calculations presented in this application. FIG. 6 shows a piezo transducer circuit having a transducer 50 connected to a series of operational amplifiers, resistors and capacitors in accordance with the figure. The circuit terminates in an analog output 52 for connection to the "E" connection shown in the middle left side of FIG. 9D in U.S. Pat. No. 5,372,136. FIG. 11, on the other hand, shows a pressure transducer circuit having a pressure transducer made 62 connected to a series of operational amplifiers, a capacitor, resistors and variable resistors as shown in the figure. The circuit terminates in an analog output also connected to the aforementioned "E" connection.

Referring more specifically to FIG. 6, a crystal oscillator is connected to ground and to the non-inverting input of a first operational amplifier, which may be an LM158. The non-inverting input of the first operational amplifier is connected to ground by a 0.047 μF capacitor C3. The first operational amplifier's feedback path to its inverting input includes a 470 K resistor R8. The first operational amplifier is suitably biased at the junction of a 220 Ω resistor R7 and a 150 μF capacitor C4 that are connected between VCC and ground.

A second operational amplifier, which may also be an LM 158, receives the output of the first operational amplifier at its inverting input via a 10 KΩ resistor R5. The second operational amplifier's non-inverting input is connected to several locations:

- to a voltage VB51, which may be 4.096 volts, through a 10 KΩ resistor R2;
- to a middle node of a voltage divider, the voltages divider extending between the non-inverting input of the first operational amplifier via a 10 MΩ resistor R4 to the middle node, and via a 10 KΩ resistor R1 to ground;
- to the inverting input of the first operational amplifier via a 10 KΩ resistor R9; and
- to ground via a 220 μF capacitor C5.

The second operational amplifier's feedback path to its inverting input includes a parallel arrangement of a 0.1 μF capacitor C2 and a 47 KΩ resistor R6. The second operational amplifier drives the A/D output 52 via a 10 KΩ resistor R3, the output connected to ground via a 1 μF capacitor C1.

Of course, the particular choice, arrangement and values of components shown in FIG. 6 may be varied while still remaining within the scope of the invention.

Referring now to FIG. 10, first through fourth operational amplifiers, which may be LM348s, are illustrated. The operational amplifiers are powered and biased by voltages VCC and VEE.

The first operational amplifier's non-inverting input is set to a value determined by the tap setting of a 1 KΩ adjustable resistor R2 that extends between VCC and VEE. The DAC input drives the first operational amplifier's inverting input via a 1 KΩ resistor R1. The first operational amplifier's feedback path includes a 50 KΩ adjustable resistor R4. The first operational amplifier drives the second operational amplifier's inverting input through an 11 KΩ resistor R3. The feedback path to the inverting input of the second operational amplifier includes a 100 Ω resistor R5.

A transducer 62, which may include a Motorola MPX20100P, has opposite terminals that drive the non-inverting inputs of the second and third operational amplifiers, respectively. The other two opposite terminals of the transducer are connected to VCC and ground, respectively.

The second operational amplifier drives the inverting input of the third operational amplifier via a 750 Ω resistor R6. The third operational amplifier's feedback path to its inverting input includes a parallel arrangement of a 93.1 KΩ resistor R10 and a 0.001 μF capacitor C1.

The third operational amplifier drives the non-inverting input of the fourth operational amplifier via a 1 KΩ resistor R7. The inverting input of the fourth operational amplifier is connected to ground via a 1 KΩ resistor R8. The feedback path to the inverting input of the fourth operational amplifier includes a 50 KΩ adjustable resistor R9. The fourth operational amplifier drives the output of the FIG. 11 circuit.

Of course, the particular choice, arrangement and values of components shown in FIG. 10 may be varied while still remaining within the scope of the invention.

C. Preferred Embodiment

Physical embodiments as shown in FIG. 1 include the optical array, pressure transducer/balloon system and clamshell fixture. Requisites of the preferred embodiment include a holder for the finger (or other tissue) such as seen in FIGS. 1 and 1A and 1B. This clam-shell fixture not only secures the tissue but also the optical array, and transducer system.

FIG. 1D is a schematic diagram for a mylar base member 38 that is shaped generally like a cross. As oriented in FIG. 1D, vertically extending portion 52 crosses with a horizontally extending portion 54 to yield top leg 56, bottom leg 58, and side legs 60, 62. In use, a finger 7 lies along the longitudinally extending portion 52 with the finger tip placed on the top leg 56 to properly cover the arrangement of LED's 32 and photodetector 34, which are arranged like those on FIGS. 1A–1C. A piezoelectric pressure transducer or strain gage 66 spans the horizontally extending portion 54 from near the tip of side leg 60 to the tip of side leg 62. In this orientation, the transducer or gage may be wrapped around the finger 7 for use in measurements.

The optical array 30, seen in FIG. 1D, shows the arrangement of multiple LED's 32 spaced at known separation distances from the detector 34. This array provides for the instantaneous distance, or "d", derivative, by the transmission mode shown in FIG. 1A or in reflectance modes shown in FIGS. 1B and 1C. However, as shown in FIG. 1E, a single LED 42 swept across the finger 7 or tissue surface 9 with a stepper motor 44 would provide a d derivative as would a cantilevered clam-shell with an angular measurement device. In any case, d must be known and/or fixed. Also the detectors and emitters may be placed anywhere about the finger.

The pressure/balloon, strain gage, or peizo transducer system incorporated within the clam-shell fixture (see Section III, A, B, C and FIG. 1A) provides the contact surface area needed to define the $\partial X_b/\partial t$.

High-speed sampling provides for a closer approximation of the instantaneous time, t, derivative, $\partial/\partial t$, as opposed to peak-valley values, see FIG. 8. Therefore, the above embodiments allow for the direct measurement of ln (i) at $d_1$, $d_2$, $d_3$ and $d_4$ cotemporaneously, thereby determining the actual α of the sampled tissue. Likewise $(\partial i/\partial t)/i$ can be directly measured at $d_1$, $d_2$, $d_3$ and $d_4$, cotemporaneously during the pulse which determines the instantaneous $\partial \alpha/\partial t$.

The above mentioned optical array can be utilized transmissively and/or reflectively provided the separation distance between the detector and first emitter ($d_1$) is greater than 3 mm.

D. Choice of Non-Ionizing Wavelengths

Since hematocrit is an example of the desired biological constituent concentration value of interest, selection criteria of the preferred wavelength must include an understanding of equation (5). That is, a wavelength whose coefficients $K_s$, $K_w$, $K_p$ are small compared to $K_b$ and which are also insensitive to oxygen saturation status must be selected. Such wavelengths include 805 nm, 590 nm, 569 nm and other isobestic wavelengths with negligible water absorption. While non-isobestic wavelengths, with small water absorption, could function, a second wavelength is needed to null out the oxygen saturation effects.

If the desired biologic constituent value of interest is the blood glucose, bilirubin, cholesterol or other parameters, then a second wavelength must be chosen. The first wavelength, 805 nm, is used to measure the hematocrit, H, after which a $K_{p805}$ (the absorbance of plasma at λ=805 nm) can be determined. Then, knowing the H, a second wavelength, 570 nm, is chosen where $KS_{p570}$ is less than $K_{p805}$. Similarly, if the first wavelength used to measure the H and the reference glucose, $K_p$ (glucose) is 570 nm, the second wavelength, 1060 nm, is chosen where $K_{p570}$ is much less than $K_{p1060}$. In the case of bilirubin, the first wavelength used to measure the H and the reference bilirubin, $K_p$ (bilirubin), is 570 nm, the second wavelength, 440 nm, is then chosen when $K_{p570}$ is much less than $K_{p440}$. The selection of these above mentioned wavelengths therefore assures uniqueness for the measurement of the desired biologic constituent.

Additionally for glucose determination, recall that the 1300 nm wavelength is not hematocrit or hemoglobin dependent but will be glucose sensitive. This is primarily due to the dependence of the scattering coefficient on the difference between the index of refraction of pure water and glucose, i.e.: recall $S_{b8}=H(1-H)\sigma_{s8}$ (from equation 7) where:

$\sigma_{s8}=8\pi^2\eta_0^2(\eta'_8-1)^2 \cdot b^v/\lambda^2$ where $\eta'_8$=index of refraction of the RBC hemoglobin at 800 nm relative to plasma $\eta_0$ (the plasma index of refraction), and, $S_{b13}=H(1-H)\sigma_{s13}$ (also from equation 7) where:

$\sigma_{s13}=8\pi^2\eta_0^2(\eta'_{13}-1)^2 \cdot b^v/\lambda^2$ $\eta'_{13}$=the index of refraction of glucose at 1300 nm relative to $\eta_0$. Therefore, the 8 13 ratio has both hematocrit and glucose information. Whereas the as $\alpha_8 \cdot \alpha'_8/\Delta P$ (equation 18a) ratio has only hematocrit information. Therefore the differential combination of those ratios will be a strong function of glucose only.

E. Improved Accuracy Pulse Oximeter Device

The accuracy of present day pulse oximeters suffers from 4 major problems: tissue perfusion (low $X_b$ and low $\partial X_b/\partial t$), d dependence (varying finger sizes), tissue nonhomogeneity (the tissue penetration depth for 660 nm light is not the same as for 940 nm light), and H dependence (see equation (5)).

All of the above mentioned deficiencies in pulse oximetry can be eliminated by understanding equation (13). Equation (13) indicates an "offset term", $$-\frac{1}{A}\frac{\partial A}{\partial X_b}.$$

Hence, while merely dividing $(\alpha i/i)_{\lambda 1}$ by $(\Delta i/i)_{\lambda 2}$ mitigates the effect of $\partial X_b/\partial t$, the d's do not completely cancel, thereby yielding the above mentioned problems. To improve pulse oximeter accuracy, a derivative is needed as in (14), which eliminates the "offset term". Hence, the ratio of $(\partial \alpha/\partial t)_{805}/(\partial \alpha/\partial t)_{660}$ results in no H, d, or $X_b$ dependence and the use of the multiple LED array and high-speed sampling as mentioned in section IV qualifies the tissue as homogeneous.

V. A Simplified Two Step Approach (A) Determination of H and $X_b$

Figure 12:
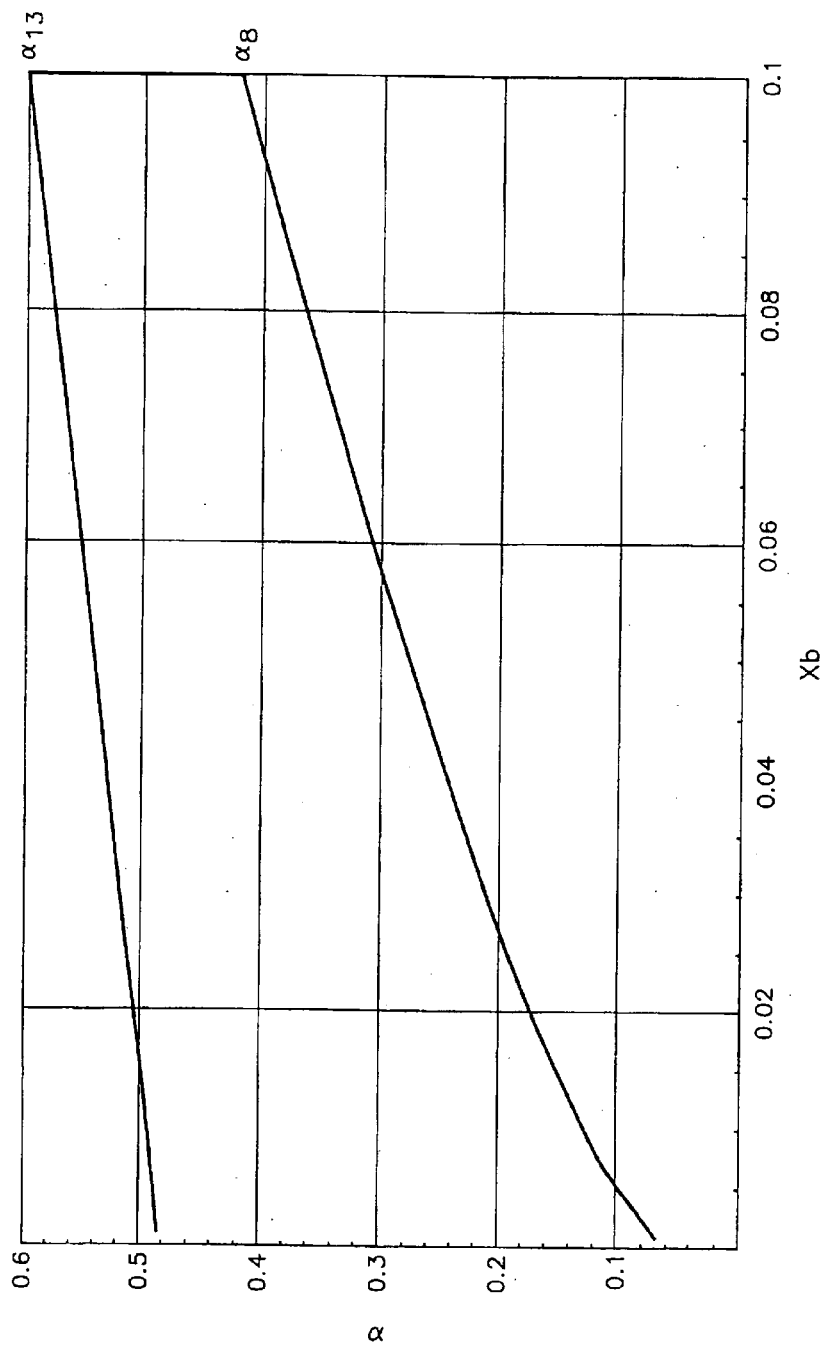
FIG. 12 plots $\alpha$ versus $X_b$ at a fixed Hematocrit.

The bulk attenuation coefficient, $\alpha$, can be easily measured with the optical array, at 805 nm, utilizing equation (10) and as described in Section IV(C). Notice that at 805 nm, $\alpha$ is a strong function of H and $X_b$ since $K_{s8}$, $K_{w8}$, $K_{p8}$ are small, see FIG. 12.

Therefore, by knowing $X_b$ itself, H can be determined. $X_b$ itself can be determined using a strain gage in the following two step approach. Step One, measure the strain gage resistance when the finger is made bloodless, by squeezing finger, such as with a stepper motor. Step Two, measure the strain gage resistance when the finger is blood filled, for example by suction. Mathematically, at 805 nm and when $K_s$, $K_p$, $K_w$, are small, equation (3) is approximated by:

$\alpha^2 \approx 3KS$ (36)

or $\alpha^2 \approx 3[K_b X_b][S_b X_b + S_s X_s]$ (37)

Substituting (5) and (7) into (37) yields:

$$0 = 3\left[H\frac{\sigma_a}{V}X_b\right]\left[H(1-H)(1.4-H)\frac{\sigma_s}{V}X_b+S_s X_s\right]-\alpha^2 \quad (38)$$

With $X_b$ and $\alpha$ measured and known, and with the $\sigma$'s and $S_s$, $X_s$ approximately constant, H can be solved with a quadratic formula or a polynomial fit. The strain gage determination of $X_b$ is as follows:

Let $V_o$=the volume of a bloodless finger. Let $V_f$=the volume of blood filled finger, and again considering the finger as a cylinder:

$V_o=\pi r^2 z = V_s+V_w$ (39)

$V_f=\pi R^2 z = V_b+V_s+V_w$ (40)

and $$\frac{V_o}{V_f}=\left(\frac{r}{R}\right)^2 \quad (41)$$

From equation (20)

$$X_b = \frac{V_f-V_o}{V_f} = 1-\frac{V_o}{V_f} \quad (42)$$

Substituting (41) into (42):

$$X_b = 1-\left(\frac{r}{R}\right)^2 \quad (43)$$

Where the strain gage resistances are proportional to the radius, r and R, of the finger.

(B) Determination of Tissue Water Content $X_w$

Choosing the wavelength of 1300 nm, where $K_s$ and $K_w$ are significant, the tissue water content, $X_w$, can be determined. Recall that $1-X_b-X_w=X_s$ and substituting into (3) yields:

$$\alpha_{13}^2 = 3(\{K_b-K_s\}X_b+\{K_w-K_s\}X_w+K_s) \quad (44)$$

$([\{K_b-K_s\}+\{S_b-S_s\}]X_b+$ $[\{K_w-K_s\}-S_s]X_w+(K_s+S_s))$

With $\alpha_{13}$, $X_b$ and H determined and because $K_b$, $K_s$, $K_w$, $S_b$, and $S_s$ are known coefficient values at 1300 nm, $X_w$ is solved with either a quadratic formula or a polynomial fit.

Results

Figure 13:
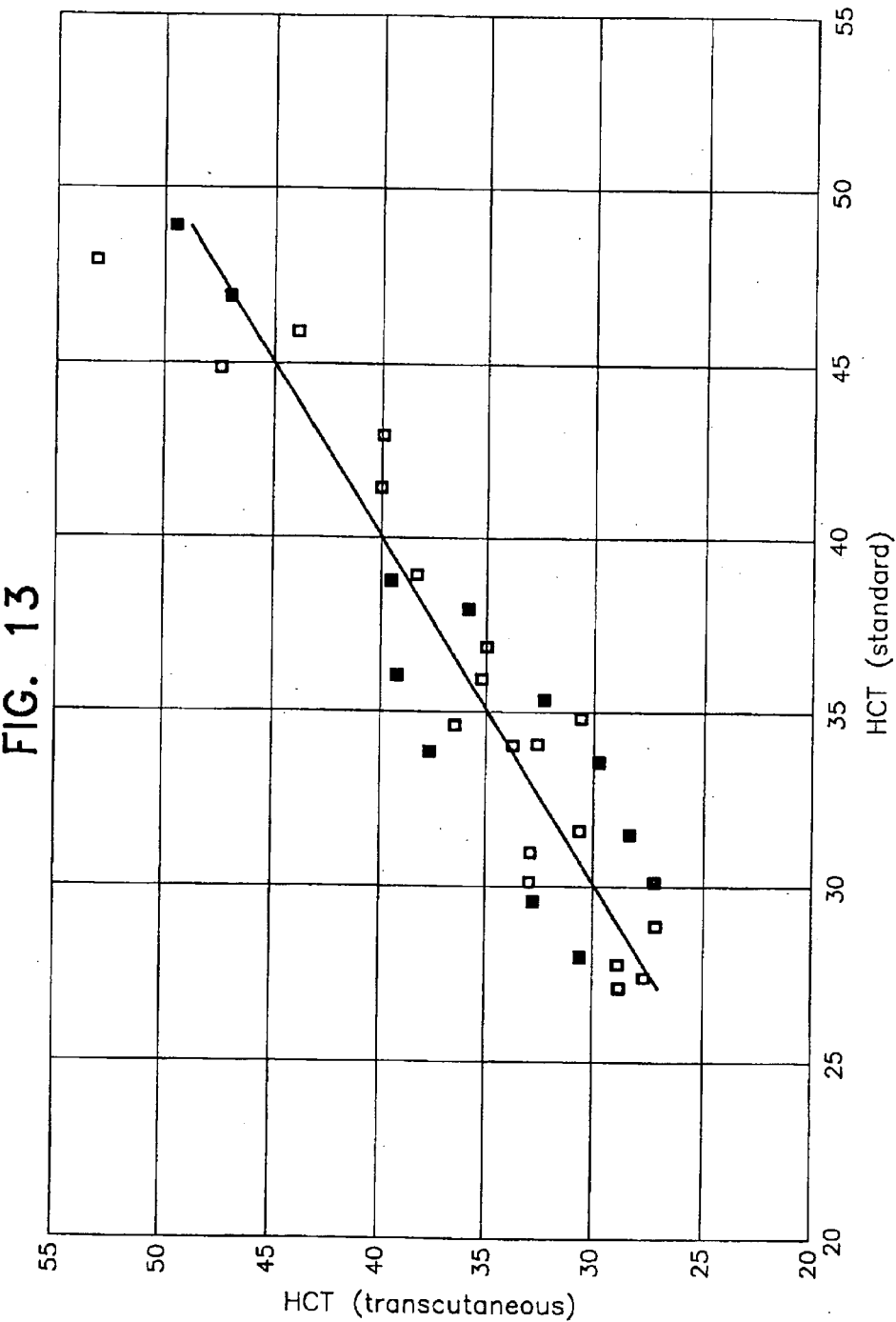
FIG. 13 gives the patient data of the new transcutaneous Hematocrit method and system plotted versus the measured Hematocrit standard.

FIG. 13 demonstrates preliminary results with 30 patients the application of the method and apparatus and the application of Equation 19 on numerous patients with a correlation of r=0.96.

As implied throughout, those skilled in the art will also appreciate that the methods for determining blood hematocrit values within the scope of the present invention may be adapted for determining other non-hematocrit biologic constituent values such as glucose, bilirubin, cholesterol, tissue water, etc.

The present invention may be embodied in other specific forms without departing from its spirit or essential characteristics. While the foregoing described embodiments are to be considered in all respects only as illustrative of the claimed invention, they are not intended to restrict the scope of the claims. The scope of the invention is, therefore, indicated by the following appended claims rather than by the foregoing description. All changes within the meaning and range of equivalency of the claims are to be embraced within their scope.

What is claimed is:

1. Apparatus for determining a desired biologic constituent concentration of the blood of a patient when the blood is flowing in a pulsatile fashion in a body part of the patient so as to be subjectable to transcutaneous examination in the body part, the body part defining a blood conduit, the comprising:
   (a) a blood conduit receiver for receiving the blood conduit with the blood flowing therein;
   (b) radiation-directing means for directing radiation into the flowing blood within the blood conduit, the radiation-directing means being situated within the blood conduit receiver, the radiation defining a directed radiation comprising a first quantity of radiation at a chosen radiation wavelength that, when directed into the flowing blood within the blood conduit, has:
      (A) a first attenuation value that varies with the desired biologic constituent concentration in the flowing blood and
      (B) a second attenuation value that varies with the concentration of components other than the desired biologic constituent in the flowing blood, which second attenuation value is at least ten times smaller than the first attenuation value, and
   (c) radiation-detecting means for detecting the portion of the directed radiation that passes through both the blood conduit and the flowing blood therein, the radiation-detecting means being situated within the blood conduit receiver, the detected portion of the directed radiation comprising a second quantity of radiation at the chosen radiation wavelength;
   (d) energy-detecting means for detecting energy from the flowing blood within the blood conduit and for measuring the time rate of change of blood volume, the energy-detecting means being situated within the blood conduit receiver, the energy defining a transduced energy comprising a quantity of energy which when detected from the flowing blood within the blood conduit, has a value that varies with the normalized change of the pulsatile blood; and
   (e) operating means for operating exclusively on the second quantity of the radiation and the transduced energy to determine the desired biologic constituent concentration.

2. The apparatus as defined in claim 1, wherein the energy-detecting means includes:
   (a) means for determining the intensity of the radiation wavelength; and
   (b) means for determining a radiation wavelength pulsatile value representing the intensities of a pulsatile component of the radiation wavelength at discreet time intervals during the pulse.

3. The apparatus as defined in claim 1, wherein the energy-detecting means includes:
   (a) means for determining the electronic signal generated from the transduced energy; and
   (b) means for determining a transduced energy pulsatile value representing the intensities of a pulsatile component of the transduced energy at discreet time intervals during the pulse.

4. The apparatus as defined in claim 1, wherein the operating means includes:

(a) means for mathematically operating on the second quantity of the radiation such that the time derivative of the pulsatile intensities is normalized by the average intensity over the pulse interval followed by a distance derivative of that quantity to produce a value proportional to $\partial\alpha/\partial t$; and
   (b) means for mathematically operating on the second quantity of the radiation such that the logarithm of the intensity is distance differentiated to produce the value $\alpha$.

5. The apparatus as defined in claim 1, wherein the operating means includes means for performing the time derivative of the normalized pulsatile transduced energy to obtain the value $\partial X_b/\partial t$, where $X_b$ is the fractional volume of blood per total tissue volume and t is time.

6. The apparatus as defined in claim 1, wherein the operating means includes means for mathematically solving the relationship $K_b = B \cdot (\alpha \cdot \partial\alpha/\partial t)/(\partial X_b/\partial t)$ with a polynomial function or empirically determined value, where $K_b$ is the macroscopic absorption coefficient for whole blood, $\alpha$ is the bulk attenuation coefficient of the tissue sample, t is time, and $X_b$ is the fractional volume of blood per total tissue volume.

7. The apparatus as defined in claim 1, wherein the desired biologic constituent comprises hematocrit or hemoglobin.

8. The apparatus as defined in claim 1, wherein the first attenuation value of the directed radiation from the radiation-directing means is substantially the same amount for oxyhemoglobin and for reduced hemoglobin in the flowing blood and the second attenuation value of the directed radiation from the radiation-directing means is at least ten items smaller than the first attenuation value for any competing constituent in the flowing blood.

9. The apparatus as defined in claim 1, wherein the radiation wavelength of the directed radiation from the radiation-direction means is in the range from about 790 nanometers to 850 nanometers.

10. The apparatus as defined in claim 1, wherein the radiation wavelength of the directed radiation from the radiation-directing means is in the range from about 550 nanometers to 600 nanometers.

11. The apparatus as defined in claim 1, wherein the energy-detecting means is selected from the group consisting of a pressure transducer element, a strain gage element, a piezo-electric film element, and a Doppler detection element.

12. Apparatus for determining a desired biologic constituent concentration of the blood of a patient when the blood flowing in a pulsatile fashion in a body part of the patient so as to be subjectable to transcutaneous examination in the body part, the body part defining a blood conduit, the apparatus comprising;
   (a) a blood conduit receiver for receiving the blood conduit with the blood flowing therein;
   (b) radiation-directing means for directing radiation into the flowing blood within the blood conduit, the radiation-directing means being situated within the blood conduit receiver, the radiation defining a directed radiation comprising:
      (i) a first quantity of radiation at a first radiation wavelength that, when directed into the flowing blood within the blood conduit, has:
         (A) a first attenuation value that varies with the desired biologic constituent concentration in the flowing blood and
         (B) a second attenuation value that varies with the concentration of components other than the desired biologic constituent in the flowing blood, which second attenuation value is at least ten times smaller than the first attenuation value, and (ii) a first quantity of radiation at a second radiation wavelength, distinct from the first wavelength, that, when directed into the flowing blood within the blood conduit, has:

(A) a third attenuation value which for varying concentrations in the flowing blood of the desired blood constituent is a non-fixed multiple of the first attenuation value; and (B) a fourth attenuation value that varies with the concentration of components other than the desired biologic constituent in the flowing blood, which fourth attenuation value is at least ten times greater than the second attenuation value;

(c) radiation-detecting means for detecting the portion of the directed radiation that passes through both the blood conduit and the flowing blood therein, the radiation-detecting means being situated within the blood conduit receiver, the detected portion of the directed radiation comprising:

(i) a second quantity of radiation at the first radiation wavelength; and, (ii) a second quantity of radiation at the second radiation wavelength;

(d) energy-detecting means for detecting energy from the flowing blood within the blood conduit and for measuring the time rate of change of blood volume, the energy-detecting means being situated within the blood conduit receiver, the energy defining a transduced energy comprising a quantity of energy which when detected from the flowing blood within the blood conduit, has a value that varies with the normalized blood change of the pulsatile blood; and (e) operating means for operating exclusively on the second quantities of the radiations and the transduced energy to determine the desired biologic constituent concentration.

13. The apparatus as defined in claim 12, wherein the operating means includes means for performing the time derivative of the normal pulsatile transduced energy of the second radiation wavelength to obtain the value $\partial X_b/\partial t$, which is the time rate of change of blood volume.

14. The apparatus as defined in claim 12, wherein the operating means includes means for solving the relationship $f(H)=G \cdot (\alpha \cdot \partial \alpha / \partial t)$ for the first wavelength divided by $(\alpha \cdot \partial \alpha / \partial t)$ for the second wavelength with a polynomial function or empirically determined value, where H is hematocrit, G is a constant related to bulk tissue absorption and scattering, $\alpha$ is the bulk attenuation coefficient of a tissue sample, and t is time.

15. Apparatus for determining a desired biologic constituent concentration of the blood of a patient when the blood is flowing in a pulsatile fashion in a body part of the patient so as to be subjectable to transcutaneous examination in the body part, the body part defining a blood conduit, the apparatus comprising:

(a) a blood conduit receiver for receiving the blood conduit with the blood flowing therein;

(b) radiation-directing means for directing radiation into the flowing blood within the blood conduit, the radiation-directing means being situated within the blood conduit receiver, the radiation defining a directed radiation comprising a first quantity of radiation at a chosen radiation wavelength which, when directed into the flowing blood within the blood conduit, has:

(A) a first attenuation value that varies with the desired biologic constituent concentration in the flowing blood and (B) a second attenuation value that varies with the concentration of components other than the desired biologic constituent in the flowing blood, which second attenuation value is at least ten times smaller than the first attenuation value;

(c) radiation-detecting means for detecting the portion of the directed radiation that passes through both the blood conduit and the flowing blood therein, the radiation-detecting means being within the blood conduit receiver, the detected portion of the directed radiation comprising a second quantity of radiation at the chosen radiation wavelength; and (d) energy-detecting means for detecting energy from the flowing blood within the blood conduit and for measuring the time rate of change of blood volume, the energy-detecting means being situated within the blood conduit receiver, the energy defining a transduced energy comprising a quantity of energy which when detected from the flowing blood within the blood conduit, has a value that varies with the normalize blood volume; and (e) operating means for operating exclusively on the second quantity of the radiation and the transduced energy to determine the desired biologic constituent concentration.

16. The apparatus as defined in claim 15, wherein the operating means comprises means for obtaining the value $X_b$ by first measuring the transduced energy when the blood conduit is blood-filled, then later measuring the transduced energy when the blood conduit is made blood-less, where $X_b$ is the volume of blood per total tissue volume.

17. The apparatus as defined in claim 16, wherein the means for obtaining $X_b$ comprises means for solving $(V_o/V_f)-1$, where $V_o$ is the volume of a bloodless finger and $V_f$ is the volume of a blood filled finger.

18. The apparatus as defined in claim 16, wherein the means for obtaining $X_b$ comprises means for solving $(V_o/V_f)-1$ with a polynomial function, where $V_o$ is the volume of a bloodless finger and $V_f$ is the volume of a blood filled finger, and wherein the energy-detecting means comprises a pressure transducer.

19. Apparatus for determining a desired biologic constituent concentration of the blood of a patient when the blood is flowing in a pulsatile fashion in a body part of the patient so as to be subjectable to transcutaneous examination in the body part, the body part defining a blood conduit, the apparatus comprising:

(a) a blood conduit receiver for receiving the blood conduit with the blood flowing therein;

(b) radiation-directing means for directing radiation into the flowing blood within the blood conduit, the radiation-directing means being situated within the blood conduit receiver, the radiation defining a directed radiation comprising a first quantity of a radiation at a chosen radiation wavelength which, when directed into the flowing blood within the blood conduit, has:

(A) a first attenuation value that varies with the desired biologic constituent concentration in the flowing blood and (B) a second attenuation value that varies with the concentration of components other than the desired biologic constituent in the flowing blood, which second attenuation value is at least ten times smaller than the first attenuation value;

(c) radiation-detecting means for detecting the portion of the directed radiation that passes through both the blood conduit and the flowing blood therein, the radiation-detecting means being situated within the blood conduit receiver, the detected portion of the directed radiation comprising a second quantity of radiation at the chosen radiation wavelength;

(d) energy-detecting means for detecting energy from the flowing blood within the blood conduit and for measuring the time rate of change of blood volume, the energy-detecting means being situated within the blood conduit receiver, the energy defining a transduced energy comprising a quantity of energy which when detected from the flowing blood within the blood conduit, has a value that varies with the normalized change of the pulsatile blood; and (e) operating means for operating exclusively on the second quantity of the radiation and the transduced energy to determine the desired biologic constituent concentration by quantifying the tissue's homogeneity from the linearity of the distance differentiation.

20. The apparatus as defined in claim 19, wherein the operating means includes:

(a) means for mathematically operating on the second quantity of the radiation wavelength such that the logarithm of the intensity is distance differentiated to produce the value $\alpha$;

(b) means for mathematically operating on the second quantity of the radiation wavelength such that the time derivative of the pulsatile intensities is normalized by the average intensity over the pulse interval followed by a distance derivative of that quantity to produce a value proportional to $\partial\alpha/\partial t$, where $\partial\alpha/\partial t$ is the change in the bulk attenuation coefficient over time;

(c) means for mathematically determining the linearity and deviation of the logarithm of the intensity and the $(\partial i/\partial t)/i$ values versus distance, where i is light intensity and t is time; and (d) means for mathematically decoupling, isolating, and determining the individual constituent absorptive and scattering coefficients from the values of $\alpha$ (the bulk attenuation coefficient), $\partial\alpha/\partial t$, and $\partial X_b/\partial t$ (the change in blood volume over time).

* * * * *